(12) United States Patent  (10) Patent No.: US 9,326,721 B2
Blurton et al.  (45) Date of Patent: *May 3, 2016

(54) LABOR MANAGEMENT DEVICES FOR PELVIC FLOOR SUPPORT

(71) Applicant: STETRIX, INC., Oakland, CA (US)

(72) Inventors: David D. Blurton, Whiteville, TN (US); Mark Buchanan, Atoka, TN (US)

(73) Assignee: STETRIX, INC., Oakland, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/806,106

(22) Filed: Jul. 22, 2015

(65) Prior Publication Data

US 2015/0320355 A1 Nov. 12, 2015

Related U.S. Application Data

(63) Continuation of application No. 14/543,251, filed on Nov. 17, 2014, now Pat. No. 9,089,301, which is a continuation of application No. 14/195,070, filed on Mar. 3, 2014, now Pat. No. 8,888,719, which is a continuation of application No. 13/833,189, filed on Mar. 15, 2013, now Pat. No. 8,684,954.

(60) Provisional application No. 61/782,814, filed on Mar. 14, 2013.

(51) Int. Cl.
*A61B 5/00* (2006.01)
*A61B 17/42* (2006.01)
(Continued)

(52) U.S. Cl.
CPC .............. *A61B 5/435* (2013.01); *A61B 5/0004* (2013.01); *A61B 5/4343* (2013.01); *A61B 5/4356* (2013.01); *A61B 5/486* (2013.01); *A61B 5/4836* (2013.01); *A61B 5/6831* (2013.01); *A61B 5/6838* (2013.01); *A61B 5/6843* (2013.01); *A61B 5/742* (2013.01); *A61B 5/7455* (2013.01); *A61B 5/7475* (2013.01); *A61B 17/42* (2013.01); *A61B 19/5202* (2013.01); *A61F 5/0093* (2013.01); *A61F 6/08* (2013.01); *A61B 5/0053* (2013.01); *A61B 5/4255* (2013.01);
(Continued)

(58) Field of Classification Search
CPC .... A61B 5/435; A61B 5/4343; A61B 5/4346; A61B 17/42; A61B 5/0053
See application file for complete search history.

(56) References Cited

U.S. PATENT DOCUMENTS 1,511 A 3/1840 Truss
316,903 A 4/1885 Lytle
(Continued)

FOREIGN PATENT DOCUMENTS

CA 2024655 A1 3/1992
CH 337982 A 4/1959
(Continued)

OTHER PUBLICATIONS

Sharp, U.S. Appl. No. 60/744,017, filed Mar. 31, 2006.
(Continued)

*Primary Examiner* — Max Hindenburg
(74) *Attorney, Agent, or Firm* — Haynes and Boone, LLP

(57) ABSTRACT

The present disclosure provides devices for decreasing the incidence of Cesarean childbirth by managing the labor process. In one aspect, a tactile feedback device is positioned adjacent the perianal tissues. A perianal support device includes a perianal support member having a pressure surface configured for engagement with tissue adjacent an anal orifice and a pressure detecting system associated with the perianal support member to detect pressure indicative of pressure on the perianal tissue of a patient.

30 Claims, 19 Drawing Sheets

(51) Int. Cl.
*A61F 5/00* (2006.01)
*A61B 19/00* (2006.01)
*A61F 6/08* (2006.01)
*A61B 17/00* (2006.01)

(52) U.S. Cl.
CPC .... *A61B 5/6823* (2013.01); *A61B 2017/00017* (2013.01); *A61B 2017/00115* (2013.01); *A61B 2560/0412* (2013.01); *A61B 2562/0247* (2013.01)

(56) References Cited

U.S. PATENT DOCUMENTS

| | | |
|---|---|---|
| 412,999 A | 10/1889 | Turney |
| 453,880 A | 6/1891 | Coffee |
| 504,598 A | 9/1893 | Leyda |
| 572,465 A | 12/1896 | Woolfolk et al. |
| 798,367 A | 8/1905 | Smokey |
| 800,071 A | 9/1905 | Cheatham |
| 811,167 A | 1/1906 | Paddock |
| 930,768 A | 8/1909 | Kelly |
| 933,610 A | 9/1909 | Yanowsky |
| 940,576 A | 11/1909 | Barnes |
| 942,590 A | 12/1909 | Sanborn |
| 964,309 A | 7/1910 | Parrott |
| 969,134 A | 8/1910 | Cowie |
| 1,031,841 A | 7/1912 | Eblen |
| 1,195,931 A | 8/1916 | Sowell |
| 1,228,384 A | 6/1917 | Agerton |
| 1,249,195 A | 12/1917 | Raines |
| 1,463,177 A | 7/1923 | Scholz |
| 1,529,937 A | 3/1925 | Turcotte |
| 1,543,632 A | 6/1925 | Louis |
| 1,565,808 A | 12/1925 | Levy |
| 1,711,294 A | 4/1929 | Weitzner |
| 1,983,636 A | 12/1934 | Palkens |
| 2,009,655 A | 7/1935 | Freymann |
| 2,073,094 A | 3/1937 | Bugh |
| 2,104,699 A | 1/1938 | O'Dell |
| 2,282,021 A | 5/1942 | Benningfield |
| 2,327,671 A | 8/1943 | Rupprecht |
| 2,468,348 A | 4/1949 | Shore |
| 2,597,637 A | 5/1952 | Hermann |
| 2,653,599 A | 9/1953 | Bell |
| 2,719,568 A | 10/1955 | Webb |
| 2,840,822 A | 7/1958 | Ericsson |
| 2,981,255 A | 4/1961 | Heyns |
| 3,101,718 A | 8/1963 | Rocker |
| 3,103,316 A | 9/1963 | Schaal |
| 3,116,735 A | 1/1964 | Geimer |
| 3,207,160 A | 9/1965 | Heyns |
| 3,216,423 A | 11/1965 | Blonsky et al. |
| 3,452,362 A | 7/1969 | Korolick et al. |
| 3,554,190 A | 1/1971 | Kaplan |
| 3,712,300 A | 1/1973 | Davidowitz |
| 3,826,242 A | 7/1974 | Eggers |
| 3,939,842 A | 2/1976 | Harris |
| 4,239,037 A | 12/1980 | Fausone |
| 4,240,436 A | 12/1980 | Singleton |
| 4,263,914 A | 4/1981 | Pawlak |
| 4,270,541 A | 6/1981 | Okamoto et al. |
| 4,421,504 A | 12/1983 | Kline |
| 4,530,122 A | 7/1985 | Sanders et al. |
| 4,557,260 A | 12/1985 | Reyes, Jr. |
| 4,583,542 A | 4/1986 | Boyd |
| 4,624,258 A | 11/1986 | Stubbs |
| 4,638,806 A | 1/1987 | Bartlett |
| 4,670,419 A | 6/1987 | Uda et al. |
| 4,691,333 A | 9/1987 | Gabriele et al. |
| 4,706,661 A | 11/1987 | Barrett |
| 4,732,146 A | 3/1988 | Fasline et al. |
| 4,782,535 A | 11/1988 | Yewer, Jr. et al. |
| 4,790,314 A | 12/1988 | Weaver |
| 4,794,915 A | 1/1989 | Larsson |
| 4,822,317 A | 4/1989 | Wimmer |
| 4,825,866 A | 5/1989 | Pierce |
| 4,866,789 A | 9/1989 | Dorm |
| 4,891,847 A | 1/1990 | Baker et al. |
| 4,976,692 A | 12/1990 | Atad |
| 4,981,307 A | 1/1991 | Walsh |
| 4,995,383 A | 2/1991 | Andersson |
| 5,007,412 A | 4/1991 | DeWall |
| 5,040,524 A | 8/1991 | Votel et al. |
| 5,148,549 A | 9/1992 | Sydor |
| 5,174,281 A | 12/1992 | Lee |
| 5,178,627 A | 1/1993 | Hudock |
| 5,234,462 A | 8/1993 | Pavletic |
| 5,263,926 A | 11/1993 | Wilk |
| 5,395,301 A | 3/1995 | Russek |
| 5,405,356 A | 4/1995 | Hahn et al. |
| 5,432,951 A | 7/1995 | Yewer, Jr. |
| 5,493,735 A | 2/1996 | Rice |
| 5,569,165 A | 10/1996 | Chin et al. |
| 5,676,637 A | 10/1997 | Lee |
| 5,690,607 A | 11/1997 | Chin et al. |
| 5,695,484 A | 12/1997 | Cox |
| 5,709,650 A | 1/1998 | Colman |
| 5,800,485 A | 9/1998 | Trop et al. |
| 5,843,025 A | 12/1998 | Shaari |
| 5,924,423 A | 7/1999 | Majlessi |
| 5,928,059 A | 7/1999 | Wicks |
| 5,935,595 A | 8/1999 | Steen |
| 5,991,979 A | 11/1999 | Moore et al. |
| 6,071,175 A | 6/2000 | Working, III |
| 6,083,241 A | 7/2000 | Longo et al. |
| 6,102,271 A | 8/2000 | Longo et al. |
| 6,123,667 A | 9/2000 | Poff et al. |
| 6,142,933 A | 11/2000 | Longo et al. |
| 6,146,345 A | 11/2000 | Mignard |
| 6,159,070 A | 12/2000 | Schwartz et al. |
| D437,642 S | 2/2001 | Caballero |
| 6,364,852 B1 | 4/2002 | Lee |
| 6,428,004 B1 | 8/2002 | McQuitty et al. |
| 6,517,562 B1 | 2/2003 | Holland |
| 6,537,132 B1 | 3/2003 | Alberts |
| 6,572,541 B1 | 6/2003 | Petersvik |
| 6,623,588 B1 | 9/2003 | Rasmussen |
| 6,627,632 B2 | 9/2003 | Parks et al. |
| 6,648,842 B2 | 11/2003 | Horkel |
| 6,668,833 B2 | 12/2003 | Rhee |
| 6,710,099 B2 | 3/2004 | Cinelli et al. |
| 6,712,841 B2 | 3/2004 | Gomez |
| 6,916,494 B2 | 7/2005 | Park |
| 6,991,813 B2 | 1/2006 | Xu |
| 7,144,379 B2 | 12/2006 | Belli |
| 7,160,294 B2 | 1/2007 | Croft |
| 7,198,609 B2 | 4/2007 | Rolnick |
| 7,318,810 B1 | 1/2008 | Benson |
| 7,673,633 B2 | 3/2010 | Blurton et al. |
| 7,766,931 B2 | 8/2010 | Blurton |
| 7,850,625 B2 | 12/2010 | Paltieli et al. |
| 8,066,009 B2 | 11/2011 | Blurton et al. |
| 8,123,760 B2 | 2/2012 | Blurton |
| 8,407,824 B2 | 4/2013 | Springer |
| 8,449,481 B2 | 5/2013 | Rohde et al. |
| 8,672,910 B1 * | 3/2014 | Kaufman ............ 604/349 |
| 2001/0000731 A1 | 5/2001 | Jia et al. |
| 2001/0003157 A1 | 6/2001 | Toth |
| 2002/0072522 A1 | 6/2002 | Parks et al. |
| 2002/0147482 A1 | 10/2002 | Carter |
| 2002/0187990 A1 | 12/2002 | Parks et al. |
| 2002/0192273 A1 | 12/2002 | Buseman et al. |
| 2003/0021850 A1 | 1/2003 | Xu |
| 2003/0092969 A1 | 5/2003 | O'Malley et al. |
| 2003/0109905 A1 | 6/2003 | Mok et al. |
| 2003/0229263 A1 | 12/2003 | Connors et al. |
| 2003/0236442 A1 | 12/2003 | Connors et al. |
| 2004/0067716 A1 | 4/2004 | Wakefield |
| 2004/0076688 A1 | 4/2004 | Park |
| 2004/0088031 A1 | 5/2004 | Gomez |
| 2004/0186356 A1 | 9/2004 | O'Malley et al. |
| 2004/0217146 A1 | 11/2004 | Beck |
| 2004/0254590 A1 | 12/2004 | Hoffman et al. |
| 2005/0000003 A1 | 1/2005 | Bushelman |

(56) References Cited

U.S. PATENT DOCUMENTS

| | | |
|---|---|---|
| 2005/0049509 A1 | 3/2005 | Mansour et al. |
| 2005/0049660 A1 | 3/2005 | Croft |
| 2005/0192169 A1 | 9/2005 | Girgen et al. |
| 2005/0203565 A1 | 9/2005 | Rethy et al. |
| 2005/0204455 A1 | 9/2005 | Pelligra |
| 2005/0214327 A1 | 9/2005 | Brooks et al. |
| 2006/0025766 A1 | 2/2006 | Heinrich et al. |
| 2006/0058831 A1 | 3/2006 | Atad |
| 2006/0144897 A1 | 7/2006 | Jankowski et al. |
| 2006/0149177 A1 | 7/2006 | Root et al. |
| 2006/0153927 A1 | 7/2006 | Xu |
| 2006/0155340 A1 | 7/2006 | Schuler et al. |
| 2006/0180158 A1 | 8/2006 | McKnight et al. |
| 2006/0195146 A1 | 8/2006 | Tracey et al. |
| 2006/0195153 A1 | 8/2006 | DiUbaldi et al. |
| 2006/0198883 A1 | 9/2006 | Parks et al. |
| 2006/0200187 A1 | 9/2006 | Gude |
| 2006/0282019 A1 | 12/2006 | Hamilton |
| 2007/0011802 A1 | 1/2007 | Holland |
| 2007/0232864 A1 | 10/2007 | Sharp et al. |
| 2008/0027357 A1 | 1/2008 | Owen |
| 2009/0076337 A1 | 3/2009 | Yang et al. |
| 2010/0292615 A1 | 11/2010 | Niederberger |
| 2011/0022056 A1 | 1/2011 | Haadem |
| 2011/0144458 A1 | 6/2011 | Gauta |
| 2012/0053535 A1 | 3/2012 | Blurton et al. |
| 2012/0083798 A1 | 4/2012 | Belli |
| 2012/0109028 A1 | 5/2012 | Sheffield |
| 2012/0221012 A1 | 8/2012 | Blurton |
| 2013/0053863 A1 | 2/2013 | Juravic et al. |

FOREIGN PATENT DOCUMENTS

| | | |
|---|---|---|
| CN | 2054668 U | 3/1990 |
| CN | 2083038 U | 8/1991 |
| CN | 1055107 A | 10/1991 |
| CN | 2097619 U | 3/1992 |
| CN | 2115081 U | 9/1992 |
| CN | 2217960 Y | 1/1996 |
| CN | 2253637 Y | 5/1997 |
| CN | 2335578 Y | 9/1999 |
| CN | 2336759 Y | 9/1999 |
| CN | 2340385 Y | 9/1999 |
| CN | 2467063 Y | 12/2001 |
| CN | 2516111 Y | 10/2002 |
| CN | 2538288 Y | 3/2003 |
| CN | 2873115 Y | 2/2007 |
| CN | 2897180 Y | 5/2007 |
| CN | 2933318 Y | 8/2007 |
| CN | 200977195 Y | 11/2007 |
| CN | 200980714 Y | 11/2007 |
| CN | 201064475 Y | 5/2008 |
| CN | 201108483 Y | 9/2008 |
| CN | 201168018 Y | 12/2008 |
| CN | 201197732 Y | 2/2009 |
| CN | 101554337 A | 10/2009 |
| CN | 201333088 Y | 10/2009 |
| CN | 201394058 Y | 2/2010 |
| CN | 201492488 U | 6/2010 |
| CN | 201529140 U | 7/2010 |
| CN | 201564577 U | 9/2010 |
| CN | 201668476 U | 12/2010 |
| CN | 201734761 U | 2/2011 |
| CN | 201734762 U | 2/2011 |
| CN | 201949105 U | 8/2011 |
| CN | 202015251 U | 10/2011 |
| CN | 202027688 U | 11/2011 |
| CN | 202136401 U | 2/2012 |
| CN | 202154729 U | 3/2012 |
| CN | 202207192 U | 5/2012 |
| CN | 202409090 U | 9/2012 |
| CN | 202409091 U | 9/2012 |
| CN | 202437308 U | 9/2012 |
| CN | 202505460 U | 10/2012 |
| CN | 202637069 U | 1/2013 |
| CN | 102988102 A | 3/2013 |
| CN | 202942188 U | 5/2013 |
| CN | 202982169 U | 6/2013 |
| DE | 2739589 A1 | 3/1979 |
| DE | 202009001363 U1 | 5/2009 |
| EP | 1477197 | 11/2004 |
| GB | 1127548 A | 9/1968 |
| GB | 2288023 A | 10/1995 |
| JP | 7275309 | 10/1995 |
| JP | 2001129004 | 5/2001 |
| JP | 2001170093 | 6/2001 |
| RU | 2196491 | 1/2003 |
| WO | WO9629013 | 9/1996 |
| WO | WO9932003 | 7/1999 |
| WO | WO0141630 A2 | 6/2001 |
| WO | WO0213680 A2 | 2/2002 |
| WO | WO03053255 A1 | 7/2003 |
| WO | WO2006086785 | 8/2006 |
| WO | WO2007114982 | 10/2007 |
| WO | WO2008096953 A1 | 8/2008 |
| WO | WO2009110863 A1 | 9/2009 |
| WO | WO2011072736 A1 | 6/2011 |

OTHER PUBLICATIONS

Bryant Ruth A., "Saving the Skin From Tape Injuries", Reprinted from American Journal of Nursing, Feb. 1988, vol. 88, No. 2, 3 pages.

Dykes et al., "Effects of Adhesive Dressings on the Stratum Corneum of the Skin", Journal of Wound Care, vol. 10, No. 2 Feb. 2001, pp. 1-4.

Gerhardt, et al., "Study of Skin-Fabric Interactions of Relevance to Decubitus: Friction and Contact-Pressure Measurements", Skin Research and Technology, 2008, 14, pp. 77-88, printed in Singapore.

Goossens, et al., "Decubitus Risk: Is Shear More Important Than Pressure?" Proceedings of the IEA 2000/HFES 2000 Congress, pp. 4-700-4-703.

Jacquet et al., "A New Experimental Method for Measuring Skin's Natural Tension", Skin Research and Technology 2008; 14: pp. 1-7, printed in Singapore.

Karwoski et al., "Experiments on Peeling Adhesive Tapes from Human Forearms", Skin Research and Technology 2004; 10: pp. 271-277, printed in Denmark.

Koval et al., "Tape Blisters Following Hip Surgery", A Prospective, Randomized Study of Two Types of Tape, Investigation performed at the Hospital for Joint Diseases, New York, and Jamaica Hospital Medical Center, Jamaica, New York, pp. 1884-1887, The Journal of Bone and Joint Surgery, Inc.

Lippmann et al., "An Alternative Anesthetic Technique for the Morbidly Obese Patient Undergoing Endovascular Repair of an Abdominal Aortic Aneurysm", From the Departments of Anesthesiology and Surgery, Harbor-UCLA Medical Center, Torrance, CA, Anesth Analg 2003;97, pp. 981-983.

Loerakker, Sandra, "Aetiology of Pressure Ulcers", Eindhoven University of Technology, Dept. of Biomedical Engineering, Section Materials Technology, Div. Biomechanics and Tissue Engineering, Oct. 2007, 31 pages.

Murahata, et. al., "Preliminary Studies on the Relationship Among Peel Force, Quantitative Measures of Skin Damage and Subjective Discomfort", Skin Research and Technology 2008; 14: pp. 1-6, printed in Singapore.

Ohura et al., "Influence of External Forces (Pressure and Shear Force) on Superficial Layer and Subcutis of Porcine Skin and Effects of Dressing Materials: Are Dressing Materials Beneficial for Reducing Pressure and Shear Force in Tissues?" Wound Repair and Regeneration (2008); 16, pp. 102-107.

Sarifakioglu et al., "Dressing Spray Enhances the Adhesive Strength of Surgical Dressing Tapes", Indian Journal of Dermatology, Venereology and Leprology, printed from www.ijdvl.com/article.asp?issn=0378-6323;year=2006;volume=72;issue=5;spage=353;epage=356, on Apr. 16, 2008, pp. 1-5.

Thomas Steve, "World Wide Wounds—Atraumatic Dressings", Published Jan. 2003, printed from www.worldwidewounds.com/2003/january/Thomas/Atraumatic-Dressings.html on Jan. 22, 2009, pp. 1-10.

(56) References Cited

OTHER PUBLICATIONS

Viegas et al., "Preventing a Surgical Complication During Cesarean Delivery in a Morbidly Obese Patient: A Simple Apparatus to Retract the Abdominal Panniculus", MedGenMed Ob/Gyn & Women's Health, Medscape General Medicine, 2006;8(1):52 printed from www.medscape.com/viewarticle/518147_print, on Nov. 16, 2007, pp. 1-5.
Wang et al., "In Vivo Biomechanics of the Fingerpad Skin Under Local Tangential Traction", Journal of Biomechanics, 2007, 40(4):851-860.
Breast Forms printed from www.geocities.com/KarenSpecial/bustform.html on Jan. 9, 2008, pp. 1-11.
Canica, Dynamic Wound Stabilization, "SutureSafe" printed from www.canica.com/suturesafe.asp on Feb. 14, 2008, 2 pages.
3M Health Care 2005, "Reducing The Risk of Superficial Skin Damage Related to Adhesive Use", 2 pages.
Vascular Solutions Bringing Solutions to Vascular Medicine, "Max-Support Abdominal Retraction Belt", printed from www.vascularsolutions.com/products/max-support on Jan. 2, 2008, 1 page.
Abramowitz et al., "Epidemiology of anal lesions (fissure and thrombosed external hemorrhoid) during pregnancy and post-partum", Gynecol Obstet Fertil 2003, No. 31, 546-549.
Danel, "Magnitude of Maternal Morbidity During Labor and Delivery: United States, 1993-1997", American Journal of Public Health, Apr. 2003, vol. 93, No. 4, pp. 631-634.
International Search Report and Written Opinion of the International Searching Authority for PCT/US06/29583 dated Aug. 3, 2007.
International Search Report and Written Opinion of the International Searching Authority for PCT/US2007/068143 dated Sep. 4, 2008, 9 pages.
Madoff, Robert, et al., "American Gastroenterological Association Technical Review on the Diagnosis and Treatment of Hemorrhoids," American gastroenterological Association Clinical Practice Committee, Jan. 8, 2004, gastroenterology 2004; 126:1463-1473.
Dimmer, Christine, et al., "Squatting for the Prevention of Hemorrhoids?" Department of Science and Technology Studies, University of Wollongong, NSW 2522, Australia, Townsend Letter for Doctors & Patients, Issue No. 159, Oct. 1996, pp. 66-70, http://www.uow.edu.au/arats/sts/bmartin/pubs/96tldp.html, 18 pages.
Agency for Healthcare Research and Quality, "Strategies to Reduce Cesarean Birth in Low-Risk Women" Comparative Effectiveness Review No. 80, Pub. No. 12(13)-EHC 128-1, Oct. 2012, 16 pages.
International Search Report and Written Opinion issued for PCT/US2014/021965 dated Jun. 3, 2014, 14 pages.
International Preliminary Report on Patentability issued for PCT/US2014/021965 dated Sep. 24, 2015, 10 pgs.

\* cited by examiner

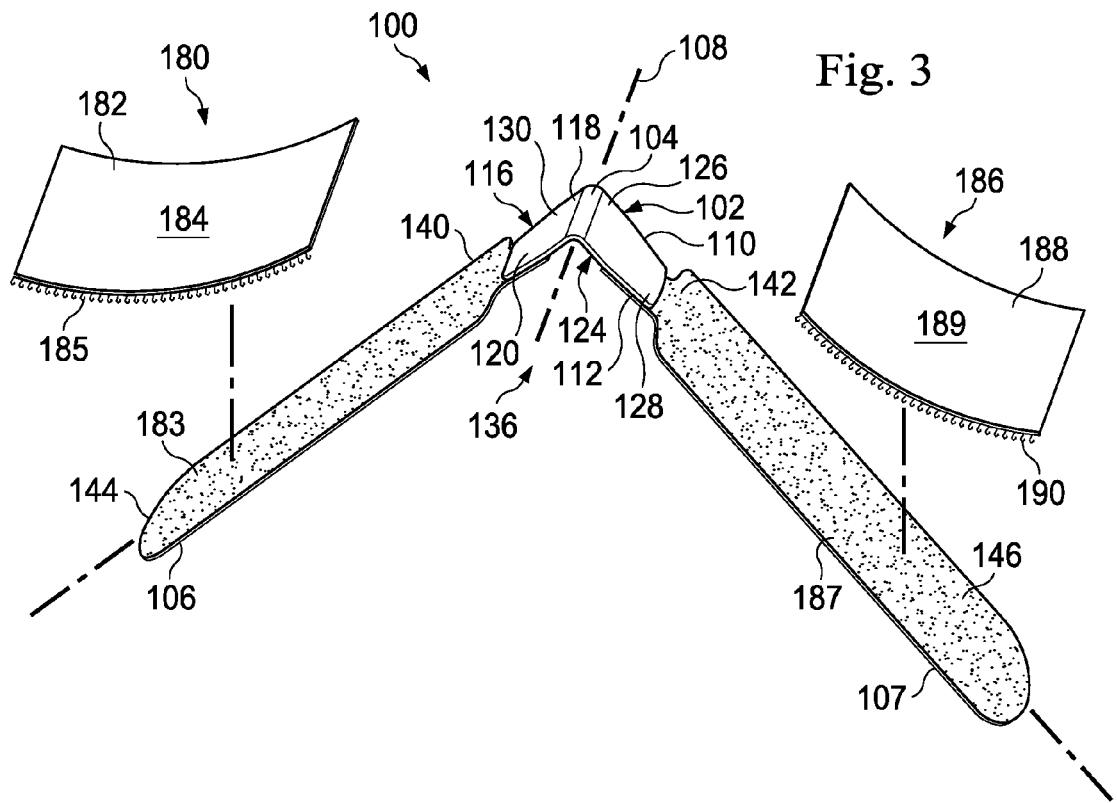
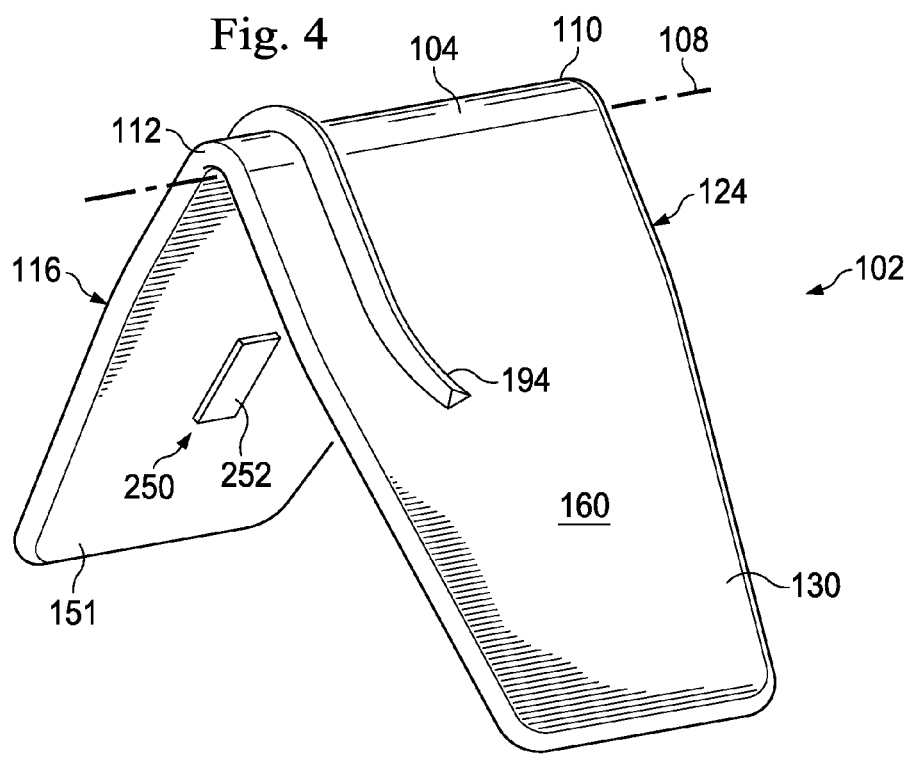

LABOR MANAGEMENT DEVICES FOR PELVIC FLOOR SUPPORT

PRIORITY

This application is a continuation of U.S. patent application Ser. No. 14/543,251, filed Nov. 17, 2014, which is a continuation of U.S. patent application Ser. No. 14/195,070, filed Mar. 3, 2014 (now U.S. Pat. No. 8,888,719), which is a continuation of U.S. patent application Ser. No. 13/833,189, filed Mar. 15, 2013 (now U.S. Pat. No. 8,684,954), which claims priority to and the benefit of the filing date of U.S. Patent Application No. 61/782,814 filed Mar. 14, 2013, titled Labor Management Devices and Methods for Decreasing the Incidence of Cesarean Childbirth, each of which is incorporated herein by reference in their entireties.

INCORPORATION BY REFERENCE

U.S. patent application Ser. No. 11/197,627 filed Aug. 5, 2005, and published as Patent Application Publication No. 2007/0031466, titled Method, Apparatus and System for Preventing or Reducing the Severity of Hemorrhoids commonly assigned to the present applicant is hereby incorporated by reference in its entirety.

U.S. patent application Ser. No. 11/743,858 filed May 3, 2007, issued as U.S. Pat. No. 7,673,633 entitled Apparatus and Method of Inhibiting Perianal Tissue Damage commonly assigned to the present applicant is hereby incorporated by reference in its entirety.

U.S. patent application Ser. No. 12/106,956 filed Apr. 21, 2008, and published as Patent Application Publication No. 2008/0202505 entitled Apparatus and Method of Supporting Patient Tissue, commonly assigned to the present applicant is hereby incorporated by reference in its entirety.

BACKGROUND

The use of epidurals and pain relieving drugs during the labor and delivery process can desensitize the birthing mother from experiencing the natural body signals needed to push the baby through the birth canal and thereby ultimately delay the progression of childbirth. One indication of this phenomenon is that in modern times, there has been a dramatic increase in the incidence of children born by Cesarean childbirth. This form of child birth significantly increases the cost to the healthcare system when compared to a natural vaginal delivery. In addition, the birthing mother needs significantly more time to recover from a Cesarean operation compared to a natural vaginal child delivery.

While prior apparatus and methods like those disclosed in U.S. Patent Application Publications 2007/0031466 and U.S. Pat. No. 7,673,633 provide stable support for the soft perianal tissues near the anal orifice, these can be further improved to provide additional benefits for labor management to decrease the incidence of Cesarean childbirth. More specifically, there are no currently available devices and methods that permit a healthcare provider to actively manage the labor and birthing process to promote a higher incidence of vaginal births and, if desired in certain situations, manage the labor process to avoid potential lifelong damage to the mother such as pelvic floor injuries and anal sphincter damage.

Thus, there is a need for devices and methods permitting the management of the child birthing process to encourage vaginal child birth to reduce the incidence of Cesarean childbirths.

SUMMARY

In one aspect, the present disclosure provides a method of decreasing the incidence of Cesarean childbirth by managing the labor process. In one aspect, a tactile feedback device is positioned adjacent the perianal tissues. A mother's labor is monitored for the progression of the baby along the birth canal. If the monitoring determines that the birthing process is not progressing as desired, the sensation offered by the tactile feedback device can be increased. In one aspect, the tactile feedback device is a pressure inducing device. In one aspect, the pressure inducing device is applied to the perianal tissue with a first pressure and then after monitoring the mother's condition, the device is repositioned to provide a second pressure on the perianal tissues. In one aspect, the second pressure is greater than the first pressure. In a further aspect, the device includes a pressure indicator and the method includes monitoring the relative pressure applied to the perianal tissue.

In still a further feature of the present disclosure, a method is provided that reduces the duration of second stage labor and delivery by allowing a healthcare provider to monitor and guide the labor process. The method includes applying a tactile feedback device in engagement with the perianal tissue and monitoring the progression of labor during the second stage. If second stage labor deviates from a predetermined time and position progress estimation, the tactile feedback device is adjusted. If the mother is below the predetermined time and position progress estimation, in one embodiment, the amount of tactile feedback is increased. In one feature, the tactile feedback device is a pressure inducing device and tactile feedback is increased by increasing the relative amount of pressure on the perianal tissue by increasing the pressure from a first initial engagement to a second higher pressure perianal tissue engagement. Such a method allows the healthcare provider to monitor the effectiveness of a mother's contractions via the impact on the perianal tissues while also providing both the healthcare provider and mother with a feedback mechanism to have a reference for turning unsuccessful contractions into effective pushes that tend to move the baby down the birth canal. In this manner, the present system and method allow cooperation between the patient and healthcare provider to allow the labor and delivery process to be managed to more quickly achieve a vaginal delivery and obviate the need for Cesarean section delivery techniques.

In yet a further feature of the present disclosure, a method is provided to inhibit the evulsion or protrusion of soft tissue adjacent the anus. The method includes positioning a blocking element adjacent the perianal tissues. The blocking element is configured to inhibit the evulsion or protrusion of soft tissue adjacent the anus. In one feature, the blocking element is initially spaced slightly from the perianal tissue such that some outward movement of the perianal tissue is permitted but upon engagement with the blocking element further outward movement by the tissue is inhibited. This engagement can increase the tactile feedback to the mother by providing a change in tactile sensation upon engagement with the blocking element. In an alternative feature, the blocking element is initially positioned in contact with the perianal tissue without providing significant pressure on the perianal tissues such that the location of the tissues are maintained but not compressed inward toward the anus of the patient. One aspect of the method allows a healthcare provider to monitor, via the blocking element, the amount of pressure applied to the blocking element by engagement with the blocking element during contractions or pushes during the birthing process.

In still a further feature of the present disclosure, a method is provided to protect a mother from pelvic floor injuries and anal sphincter damage. In one aspect, the method includes applying a blocking member adjacent the perianal tissue to inhibit evulsion or protrusion of the soft tissue. In one form, the blocking member is applied adjacent the perianal tissues in an initial non-pressure inducing engagement. The blocking member can include a pressure detection feature and the healthcare provider can monitor the pressure detector during pushing and contractions of the patient to evaluate the amount of pressure applied to the perianal tissue. If the pressure is above an upper threshold, the patient will be encouraged to reduce the extent of their efforts at pushing during contractions. However, if the pressure detection indicates a pressure below a lower threshold, the healthcare provider will encourage the patient to apply more downward pressure during contracts to more effectively push the baby down the birth canal toward the vaginal opening. In this manner, the healthcare provider can manage the mother's labor to maintain the pressure on the perianal tissues within a desired range that is safe for the mother's tissue while at the same time encouraging proficient pushing from the mother to advance the labor and delivery process to avoid stalled delivery and encourage fetal decent to achieve a vaginal child birth.

In still a further feature, a method is provided for managing the birthing process. In an initial phase, it is determined whether the mother has previously had a successful vaginal delivery. If yes, then the mother is allowed to continue with unaided labor. Even for this mother, labor is continually monitored and if the progression of labor slows, then a tactile feedback device may be applied to the perianal tissue and the method continues as set forth below. If the mother has not previously had a successful vaginal delivery, this could include first time nulliparous mothers or women attempting vaginal births after Cesarean deliveries, a tactile feedback device is applied to the perianal tissue. In one form, the tactile feedback device is applied in a pressure engagement position such that the perianal tissue is displaced inwardly and a first pressure is applied. In an alternative form, the tactile feedback device is positioned adjacent the perianal tissue without pressure such that the perianal tissue is not displaced inwardly. The mother may then be allowed to continue with an aided or managed labor process. In a further feature, the managed labor process continues with a healthcare provider receiving feedback from the device to evaluate the effectiveness of the mother's pushing efforts during contractions. If the feedback device indicates pushes above a first, minimum threshold, the mother may continue her labor efforts without change. If the feedback device indicates pushes below the first, minimum threshold, the healthcare provide will instruct the patient on techniques to channel contraction efforts into effective pushes urging the baby downward along the birth canal. If the patient continues to struggle to achieve effective pushes and labor is not progressing, then the healthcare provider may increase the pressure applied by the tactile feedback device on the perianal tissues to provide the mother with even greater tactile feedback. In one aspect, if the mother receives an epidural or other pain relieving medication, then the healthcare provide would responsively increase the pressure applied by the tactile feedback device on the perianal tissue in an effort to overcome the effects of the numbing treatment given to the mother. In still a further alternative aspect of actively managing the labor process, the healthcare provider also monitors the feedback device for pressures above a maximum pressure indication. Such high pressures may be indicators for pelvic floor injuries and anal sphincter damage. Thus, the healthcare provider may instruct the patient to reduce the pushing effectiveness during contractions to limit the pressure on the mother's delicate tissues in an effort to inhibit damage to these tissues. In an alternative feature of the present method, the healthcare provider monitors pressure applied by the tactile feedback device to maintain the pressure during contractions between the first, minimum pressure and the higher, maximum pressure to thereby balance the needs of progressing labor while simultaneously attempting to avoid lifelong injuries to the mother.

In an exemplary aspect, the present disclosure is directed to an apparatus including a perianal support member that has a pressure surface configured for engagement with tissue adjacent an anal orifice. A pressure detecting system may be associated with the perianal support member to detect pressure indicative of pressure on the tissue adjacent the anal orifice of a patient.

In an exemplary aspect, the present disclosure is directed to a method including applying a perianal support device to a perianal region of a patient; monitoring pressure in the perianal region with a feedback device associated with the perianal support device; advancing the perianal support device against the perianal region until the monitored pressure meets a first pressure threshold based on the feedback device; and securing the perianal support device in a position where the monitored pressure meets the first pressure threshold. In a further feature, the method includes monitoring the progression of labor and adjusting the pressure applied by the perianal support device in response to changes in the progression of labor, including failure of the baby to progress within the birth canal or failure of the mother's pushes to generate a sufficient change in pressure indicated by the pressure monitor. In one aspect, the pressure applied to the perianal tissue is increased if the progression of labor in slowed below a predetermined threshold allowing a healthcare provider to manage the progression of labor.

In an aspect, the method further includes utilizing the feedback device to monitor sensed pressure changes associated with contractions and alerting a user to the pressure changes. In some aspects, alerting a user includes one of activating an audible alert, activating a visual alert, and activating a material change. In some aspects, activating a visual alert includes turning a light on, off, or changing its color.

In an aspect, the method further includes alerting a user when the monitored pressure exceeds a second pressure threshold higher than the first pressure threshold.

In an aspect, the pressure detecting system comprises a strain gauge disposed on a wall portion of the perianal support member. In an aspect, the pressure detecting system comprises: a pressure detecting element configured to detect pressure applied on the tissue by the perianal support member; and a user interface configured to display information relating to the pressure detected by the pressure detecting element. In an aspect, the user interface is configured to wirelessly communicate with the pressure detecting element. In an aspect, the pressure detecting system comprises a compliant pad on a pressure surface of the perianal support member. In an aspect, wherein the compliant pad is configured to change appearance when pressure exceeds a threshold pressure. In an aspect, the perianal support member is at least partially transparent.

In a further aspect, the pressure detecting system comprises: a pressure detector; and a light associated with the pressure detector and configured to turn on when the pressure detector detects application of a therapeutic pressure on the perianal tissue. In an aspect, the pressure detector comprises a pressure switch. In an aspect, the pressure switch is configured to complete a circuit when a therapeutic pressure is applied to the perianal tissue. In an aspect, the pressure detecting system comprises: a transmitter carried on the perianal support member; and a receiver spaced apart from the perianal support member configured to receive signals from the transmitter indicative of pressure applied by the perianal support member on the perianal tissue. In an aspect, the pressure detecting system comprises a securing member extending from the perianal support member, the securing member being configured to convey information indicative of pressure applied on the perianal tissue by the perianal support member. In an aspect, the securing member comprises an element configured to change appearance when pressure changes. In an aspect, the securing member is associated with a visual indicator such as an LED indicator. In an aspect, the securing member comprises an elastically stretchable portion and at least one stretch inhibitor configured to inhibit stretch when stretching is sufficient to apply a therapeutic pressure on the perianal tissue. In an aspect, the at least one stretch inhibitor is a substantially inelastic fiber. In an aspect, the at least one stretch inhibitor is a substantially inelastic strap. In an aspect, the securing member comprises a geometric figure that takes shape when stretching is sufficient to apply a therapeutic pressure on the perianal tissue. In an aspect, the securing member comprises a strain gauge configured to measure strain as an indicator of a therapeutic pressure on the perianal tissue.

In yet another aspect, the apparatus includes a device adjustment element graspable by the patient when the perianal support member is engaged with the tissue. In an aspect, the device adjustment element comprises handle portions. In an aspect, the device adjustment element comprises: an adjustment strap extending from the perianal support member; and an anchor pad comprising a guide configured to guide movement of the adjustment strap. In an aspect, the apparatus includes a compliant pad, the pressure detecting system being disposed between the complaint pad and the perianal support member. In an aspect, the apparatus includes a compliant pad having a pocket formed therein, the pressure detecting system being disposed within the pocket. In an aspect, the perianal support member includes a cooling applicator configured to apply therapeutic cooling to the perianal tissue. In an aspect, the cooling applicator comprises a receptacle for a cooling material. In an aspect, the perianal support member is a thermal conductor. In an aspect, the cooling applicator is shaped to fit flush with the perianal support member. In an aspect, the pressure detecting system is configured to count contractions during child delivery.

In an exemplary aspect, the present disclosure is directed to an apparatus including a perianal support member having a pressure surface configured for engagement with tissue adjacent an anal orifice. A cooling applicator is configured to apply therapeutic cooling to the perianal tissue.

In an exemplary aspect, the cooling applicator comprises an ice pack. In an aspect, the cooling applicator comprises a receptacle for a cooling material. In an aspect, the perianal support device is a thermal conductor. In an aspect, the cooling applicator is shaped to fit flush with the perianal support member. In an aspect, the apparatus includes a pressure detecting system associated with the perianal support member to detect pressure indicative of pressure on the tissue adjacent the anal orifice of a patient. In an aspect, the pressure detecting system comprises a strain gauge disposed on a wall portion of the perianal support member. In an aspect, the pressure detecting system comprises: a pressure detecting element configured to detect pressure applied on the tissue by the perianal support member; and a user interface configured to display information relating to the pressure detected by the pressure detecting element. In an aspect, the user interface is configured to wirelessly communicate with the pressure detecting element.

In an aspect, the pressure detecting system comprises a securing member extending from the perianal support member, the securing member being configured to convey information indicative of pressure applied on the perianal tissue by the perianal support member. In an aspect, a device adjustment element graspable by the patient when the perianal support member is engaged with the tissue. In an aspect, the device adjustment element comprises handle portions.

In an exemplary aspect, the present disclosure is directed to an apparatus, including a perianal support member including a pressure surface configured for engagement with tissue adjacent an anal orifice. A device adjustment element is graspable by the patient when the perianal support member is engaged with the tissue.

In an aspect, the device adjustment element comprises handle portions. In an aspect, the device adjustment element comprises: an adjustment strap extending from the perianal support member; and an anchor pad comprising a guide configured to guide movement of the adjustment strap. In an aspect, the perianal support member includes a cooling applicator configured to apply therapeutic cooling to the perianal tissue. In an aspect, the cooling applicator comprises an ice pack. In an aspect, the cooling applicator comprises a receptacle for a cooling material. In an aspect, the perianal support device is a thermal conductor. In an aspect, the cooling applicator is shaped to fit flush with the perianal support member. In an aspect, the apparatus includes a pressure detecting system associated with the perianal support member to detect pressure indicative of pressure on the tissue adjacent the anal orifice of a patient. In an aspect, the pressure detecting system comprises a strain gauge disposed on a wall portion of the perianal support member. In an aspect, the pressure detecting system comprises: a pressure detecting element configured to detect pressure applied on the tissue by the perianal support member; and a user interface configured to display information relating to the pressure detected by the pressure detecting element. In an aspect, the user interface is configured to wirelessly communicate with the pressure detecting element. In an aspect, the pressure detecting system comprises a securing member extending from the perianal support member, the securing member being configured to convey information indicative of pressure applied on the perianal tissue by the perianal support member.

In an exemplary aspect, the present disclosure is directed to a method, comprising: providing a support member having a pressure surface configured for engaging the perianal area of a patient and an elongated compression element; positioning the pressure surface proximate the perianal area of a patient and the compression member extending outwardly beyond the crown of the buttocks; and detecting the pressure on the perianal area of the patient applied by the pressure surface against the perianal area of the patient.

In an aspect, detecting the pressure on the perianal area comprises detecting the pressure with a strain gauge disposed on the compression element of the perianal support member. In an aspect, the method includes displaying information relating to the detected pressure on a user interface. In an aspect, the method includes transmitting signals from the support member to the user interface. In an aspect, the method includes alerting a healthcare provider when the detected pressure detects application of a therapeutic pressure on the perianal tissue. In an aspect, alerting a healthcare provider comprises changing the color of a compliant pad. In an aspect, alerting a healthcare provider comprises turning on a light bulb. In an aspect, alerting a health care provider comprises inhibiting stretch of a securing member when stretching is sufficient to apply a therapeutic pressure on the perianal tissue. In an aspect, the method includes therapeutically cooling the perianal tissue with the support member.

In an exemplary aspect, the present disclosure is directed to a method of inhibiting perianal tissue damage during childbirth, comprising: positioning a perianal support device in contact with at least a portion of the perianal tissue of the patient prior to delivery of a child; positioning a compression member associated with the support device to extend outwardly in the saggital plane beyond a gluteal cleft; adjusting pressure applied on the perianal tissue until a pressure detecting system indicates application of a therapeutic pressure by the perianal support device.

In an aspect, adjusting pressure applied comprises pulling a device adjustment element attached to the perianal support device to increase the pressure on the perianal tissue. In an aspect, the method includes monitoring the pressure detecting system to confirm the applied pressure is above a therapeutic pressure threshold. In an aspect, the method includes detecting the pressure with a strain gauge disposed on the compression element of the perianal support member. In an aspect, the pressure detecting system displays information relating to the detected pressure on a user interface. In an aspect, the method includes therapeutically cooling the perianal tissue with the support member.

Further aspects, forms, embodiments, objects, features, benefits, and advantages of the present disclosure shall become apparent from the detailed drawings and descriptions provided herein.

BRIEF DESCRIPTION OF THE DRAWINGS

FIG. 3 is a perspective view of one aspect of the perianal support system according to an exemplary embodiment.

FIG. 4 is a perspective view of a portion of the perianal support system according to an exemplary embodiment.

DETAILED DESCRIPTION

Figure 1:
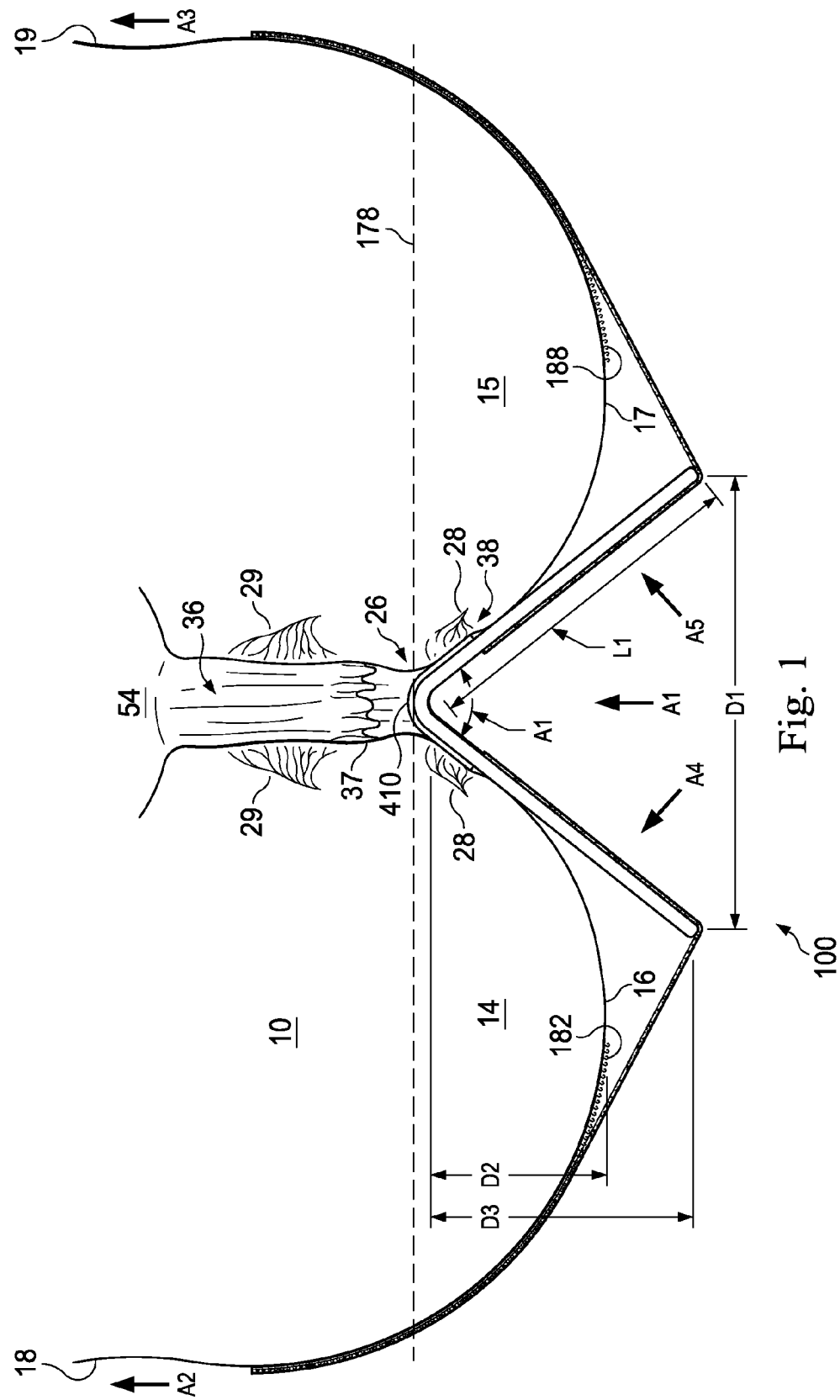
FIG. 1 is a partial cross sectional top view of a perianal support system applied to a patient with stylized depiction of the patient anatomy.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

The present disclosure is directed to systems, devices, and methods for managing child birthing labor along with supporting or treating perianal tissue of a patient. These systems introduce novel elements and methods that may improve the reliability, the predictability, and the effectiveness of labor along with supporting or treating the perianal tissues. In addition, some aspects of these systems include elements and methods that may simplify proper securing and proper placement. Some embodiments provide feedback to surgeons and patients regarding pressure levels due to device application or physiological transformations, such as those that occur during muscle contractions during child delivery. Supporting the perianal tissue of a patient during $2^{nd}$ stage labor may reduce the incidence of a number of complications and conditions, including, for example, pelvic floor incompetence or dysfunction (over-stretching of pelvic floor muscles, ligaments and tendons), organ prolapse results from the over stretching, incontinence secondary to pressure and stretching exerted on bladder and bladder neck, over stretching due to use of forceps in delivery, perineum tears and lacerations due to over stretching, forceps use, or uncontrolled flexion/extension of the fetal head as it descends, and hemorrhoids. Still further, application of pressure in the perianal region can be sensed as a tactile sensation by a patient, often even after administration of an epidural and provides a pushing focal point to enhance the effectiveness of contractions and pushing. This may result in a shortening of second stage labor by enhancing the effectiveness of contractions in advancing the baby down the birth canal. In addition, it may reduce the necessity of Cesarean section deliveries by encouraging and monitoring via pressure feedback the effectiveness of contractions to generate a pushing effect on the baby moving it toward the vaginal opening. It may also cover all or most of the anal orifice and thereby provide defecation suppression of hemorrhoid development and or advancement of existing hemorrhoids. Some embodiments may include a post-delivery therapeutics delivery system.

In some aspects, the devices and systems disclosed herein may include varying pressure detecting and monitoring capabilities. For simplicity, these are referred to herein as a) a static support pressure indication capability, b) a dynamic support pressure indication capability, and c) an extreme support pressure indication capability. The static support pressure indication capability may include detecting and monitoring pressure ranges that provide therapeutic support and push feedback. The dynamic support pressure indication capability may include detecting and monitoring pressure ranges indicative of increases in pressure level above the static pressure that provide feedback on push effectiveness. The extreme support pressure indication capability may include detecting and monitoring pressure ranges above desired pressures and may warrant adjusting the perianal support device in order to alleviate some the pressure on the patient.

Figure 2:
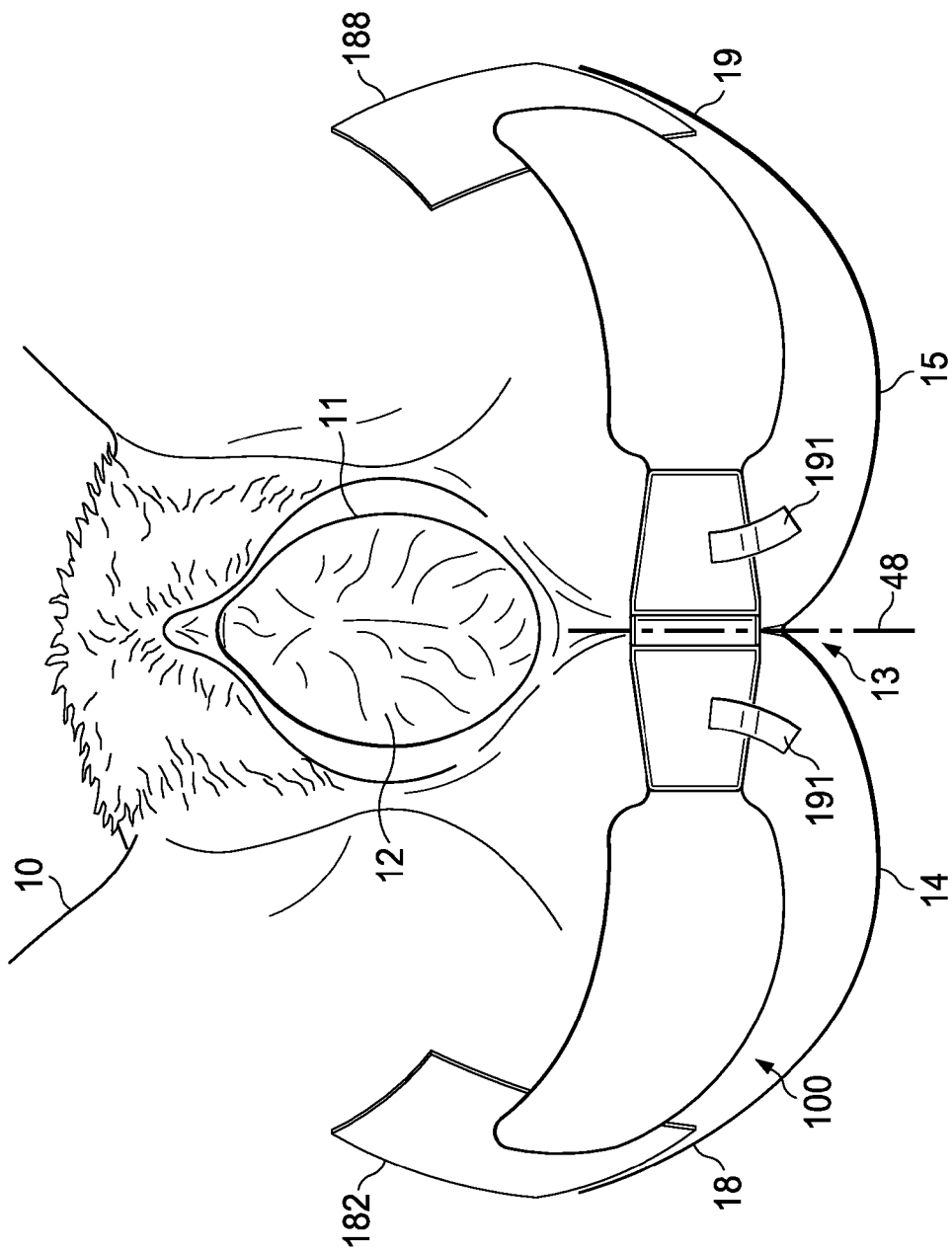
FIG. 2 is a partial perspective bottom view of the perianal support system applied to a patient during child delivery.

Turning now to FIG. 1-3, a perianal support system 100 according to one exemplary embodiment disclosed herein is illustrated in association with the perianal tissue of a patient 10. FIGS. 1 and 2 shows the perianal support system 100 in use on the patient 10 and FIG. 3 shows the support system 100 independent of the patient 10.

In FIG. 1, the patient 10 is shown in partial cross section to illustrate a portion of the rectum 54, anal canal 36, anal orifice 38, internal venous plexus 29, pectinate line 37 (also known as the dentate line), and external venous plexus 28. The patient's buttocks 14 and 15 are shown with the crown of the buttocks 16 and 17, respectively, laterally adjacent the perianal region 26. The gluteal cleft 13 (FIG. 2) is between buttocks 14 and 15. The buttocks 14 and 15 extend laterally beyond crowns 16 and 17 toward lateral flanks 18 and 19, respectively. The crowns 16 and 17 of each buttocks 14 and 15 in essence define the midline of each leg and the lateral flanks 18 and 19 are the area lateral of the leg/buttocks midline. The lateral flanks 18 and 19 may include, for example but without limitation, all or a portion of the lateral buttocks, hips, or upper thigh of the patient.

FIG. 2 illustrates the patient 10 during a child birthing process. Contractions during labor move a child 12 into the birth canal and ultimately, for a vaginal delivery, through the vaginal opening 11, as shown in FIG. 2. In an alternative birthing process, labor is commenced to move the child 12, but for a variety of reasons, the delivery does not occur vaginally but instead caesarian delivery is performed through a surgical opening in the mother's abdomen. During the birthing process, tremendous pressure is exerted in an effort to move the child toward delivery. At least some of this pressure is exerted against the tissues adjacent the anal orifice 38 in the perianal region 26 (FIG. 1). The result of these forces is that blood vessels near the anus, such as those in the external venous plexus 28, may bulge or rupture causing hemorrhoids or increasing their severity. Still further, other tissues in the perianal region 26 adjacent the anus may distend outwardly opposite arrow A1 in FIG. 1 causing lacerations such as tearing around the vaginal opening 11 or fissures from the anus. In addition to the blood loss, pain, and discomfort, these lacerations can be a location for infections in the mother.

The systems, devices, and methods disclosed herein, including the exemplary system 100, are shaped and structured to not only support the perianal tissues (tissue forming or supporting the perianal region 26) during the birthing process without interfering with the birthing canal or vaginal opening 11, but also include features, elements, or structure that simplify application to the patient by providing indicators that detect pressure or indicate when desired application pressures are achieved. Some exemplary embodiments provide feedback to surgeons and patients regarding pressure levels due to device application or physiological transformations, such as those that occur during muscle contractions during child delivery. Additional exemplary embodiments provide user adjustment systems and techniques, allowing a patient as well as a doctor to adjust the devices for comfort and effectiveness. Accordingly, the exemplary systems, devices, and methods disclosed herein support the perianal tissue to inhibit damage to the tissue near the anal orifice 38, both internally and externally, to inhibit, for example but without limitation, the formation or advancement of external hemorrhoids, and/or to inhibit the formation or advancement of lacerations of the perianal tissues.

FIG. 3 shows the support system 100 independent of the patient. The support system 100 includes a perianal support member 102 having an external pressure surface 104 and a pair of extending securing members 106, 107 attached to and configured to assist in holding the perianal support member 102 in pressurized engagement with the perianal tissue in the perianal region 26 shown in FIGS. 1 and 2. The external pressure surface 104 extends along midline axis 108 between a posterior edge 110 and the anterior edge 112 of the perianal support member.

The perianal support member 102 includes a pair of compression elements 116, 124 formed as flanges. The first compression element 116 has a distal end portion 118 adjacent the pressure surface 104 and an opposing proximal end portion 120. The opposing second compression element 124 has a distal end portion 126 adjacent the pressure surface 104 and an opposing proximal end portion 128. The perianal support member 102 includes an outer surface 130 and an opposing inner surface 132 (FIGS. 1 and 2) defining an access cavity 136.

As shown in FIGS. 1-3, the securing member 106 is attached to the first compression element 116 adjacent its proximal end portion 120. In a similar manner, the second securing member 107 is attached to the second compression member 118 adjacent its proximal end portion 128. In the illustrated embodiment, the securing members 106, 107 are elongated, flexible strips of a material. Midline end portions 140, 142 of the securing members 106, 107 attach to the compression elements 116, 118 of the perianal support member 102 while opposing lateral ends 144, 146 extend outwardly laterally from the midline or contact axis 108 of the perianal support system 100.

The first securing member 106 forms all or a part of a securing mechanism 180. In the embodiment in FIGS. 1-3, the securing mechanism 180 includes the securing member 106 and an associated anchor pad 182. In this example, the securing member 106 includes a first half of a releasable fastening system on a surface 183, such as a hook and loop system or a releasable adhesive system. In the illustrated embodiment, the anchor pad 182 has a generally square shape that is shorter in length and wider than elongated securing member 106. The shape of the anchor pad is shown for illustration purposes and may take any form that is suitable for fixing to a patient or inanimate object, as well as joining to the elongated fixation member. The anchor pad 182 includes a first surface 184 having an adhesive surface adapted for joining to the patient's skin or some inanimate object. The opposing surface 185 includes the second half of the releasable fastening system. In a similar manner, the securing member 107 forms all or part of a securing mechanism 186 and includes a releasable fastening system on surface 187, such as a hook and loop system or a releasable adhesive system. In this example, a second component of the securing mechanism 186 includes an anchor pad 188. In the illustrated embodiment, anchor pad 188 has a generally rectangular shape that is shorter in length and wider than elongated fixation member 107. The anchor pad 188 includes a first surface 189 having an adhesive surface adapted for joining to the patient's skin or some inanimate object. The opposing surface 190 includes the second half of the releasable fastening system.

In some embodiments, instead of using the hook and loop fastener arrangement discussed above, at least a portion of a surfaces 183, 187 of the securing members 106, 107 has an adhesive coating adapted for joining to a fixed object. The securing member 106 may be fixed to the inner surface 132 of the compression element 116. Likewise, the securing member 107 is joined to the proximal end portion 128 of the second compression element 124. At least a portion of a surface of the securing member includes an adhesive coating that can fix the securing member to another object. In one embodiment, the adhesive coating is adapted for releasably adhering to a patient's skin. In another embodiment, the adhesive is adapted for joining to an inanimate object or to itself. In this manner, the securing member can fix the position of the perianal support member 102 relative to the operating table or other fixture near the patient. In some embodiments, the securing members are formed of flexible tape. Further, while they have been described separately, in one embodiment, the securing members are formed by a continuous piece of material joined in the middle to the perianal support member 102.

FIG. 2 shows exemplary flip preventer straps 191 that may extend from sides at least partially in the direction of the axis 48 to reduce the likelihood that the perianal support member 102 will flip when under loading or during adjustment. In some embodiments, the flip preventer straps 191 are formed of flexible surgical tape. In other embodiments, the flip preventer straps 191 are hook and loop fastener portions that attach to anchor pads similar to the anchor pads 188, but much smaller to comfortably adhere to the body.

Figure 5:
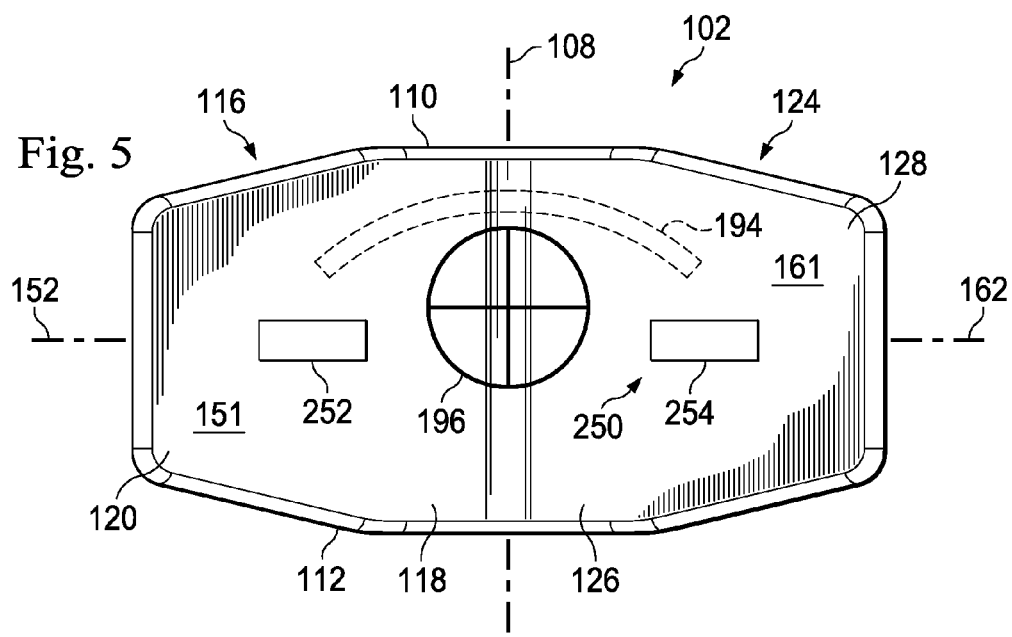
FIG. 5 is an end view of a portion of the perianal support system of FIG. 4.
Figure 6:
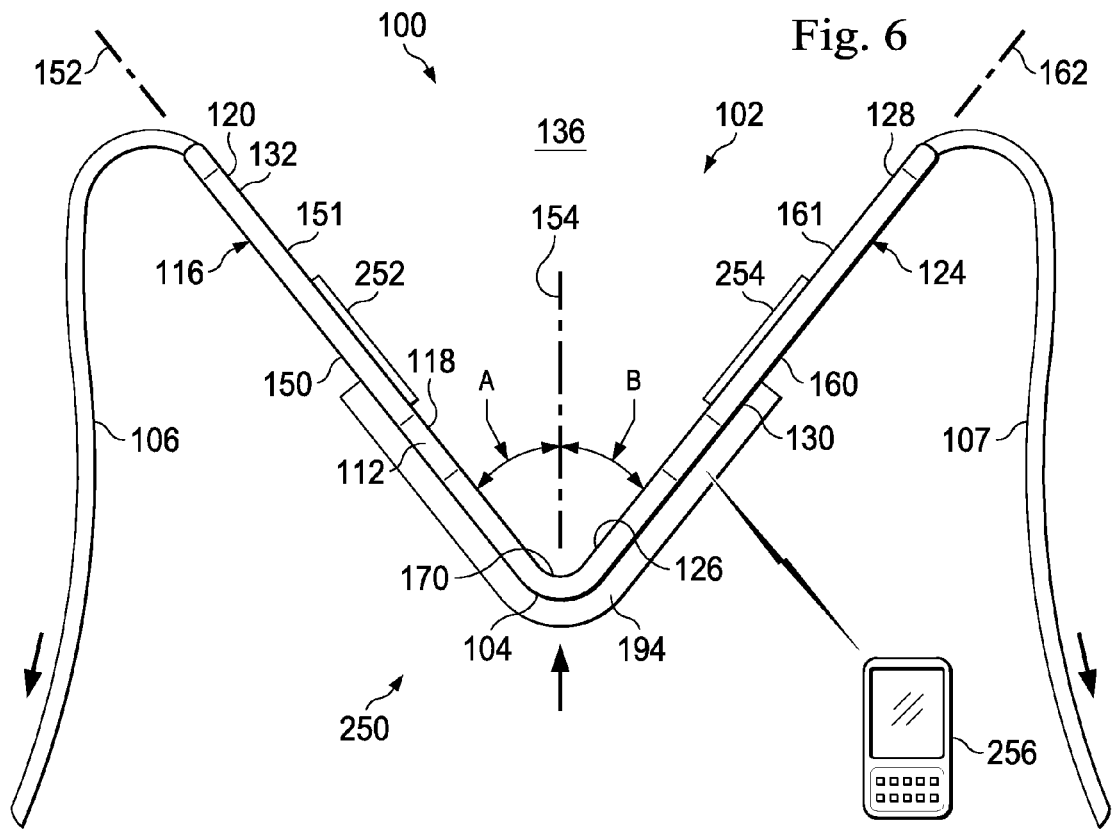
FIG. 6 is a side view of the perianal support system of FIG. 1 according to an exemplary embodiment.

The exemplary perianal support member 102 in FIGS. 1-3 is shown in greater detail in FIGS. 4-6. In the example shown the first and second compression elements 116, 124 are integral with and define a portion of the perianal support member 102. The distal end portion 118 (FIG. 5) of the compression element 116 transitions into the pressure surface 104. The compression element 116 also includes an elongated, planar exterior side wall 150 (FIG. 6) extending from the distal end 118 to the proximal end 120. The compression member 116 extends generally along axis 152 which is substantially transverse to the midline axis 108 as shown in FIG. 5. As shown in the end view of FIG. 6, the compression element 116 extends at an oblique angle A with respect to an axis 154. It will be understood that axis 154 is also representative of the saggital plane of the body and midline axis 108 extends generally within the sagittal plane. In a similar manner, the distal end 126 of the compression element 124 transitions into the pressure surface 104. The compression element 124 also includes an elongated, planar exterior side wall 160 extending from the distal end 126 to the proximal end 128. The compression element 124 extends generally along an axis 162 which is substantially transverse to the midline axis 108 as shown in FIG. 5. The end view of FIG. 6 shows the compression element 124 extending at an oblique angle B with respect to the axis 154. It will be appreciated that in the illustrated embodiment, compression element 124 extends at an oblique angle A substantially equal to the oblique angle B at which compression element 116 extends with respect to axis 154. In some embodiments, the oblique angles A and B are each within the range of about 5 to 25 degrees. In other embodiments, the oblique angles A and B are each within the range of about 10 to 20 degrees, and in yet other embodiments, are with a range of about 15 to 20 degrees.

The perianal support member 102 of the perianal support system 100 has an internal contact surface 170 defined along the midline 108 opposing the external pressure surface 104. It will be understood that a health care provider may apply pressure to the contact surface 170 to move the perianal support member 102 into the operative position shown in FIGS. 1 and 2 and/or apply additional pressure to compress at least some perianal tissue. The compression element 116 includes an interior wall 151 while the compression element 124 has an opposing interior wall 161 generally facing interior wall 151. The interior walls 151, 161, along with the internal contact surface 170 define the access cavity 136 within the perianal support device 100. As shown in FIG. 6, the configuration of the perianal support member 102 as described above results in a generally wedge shaped device. Still further, with the inclusion of the access cavity 136, the perianal support member 102 has a substantially V-shaped configuration with the pressure surface 104 defined at the apex of the V and the compression elements 116, 124 forming the legs of the V.

In this exemplary embodiment, the support system 100 includes a pressure detecting system 250. The pressure detecting system 250 may be associated and configured with other components of the support system 100, such as the perianal support member 102 or the securing members 106, 107. In some embodiments, the pressure detecting system 250 is integrally formed with components of the support system 100 discussed above. That is, in some embodiments, the pressure detecting system 250 is a part of the support system 100. In other embodiments, the pressure detecting system 250 is associated with the support system 100 in a manner enabling the pressure detecting system 250 to monitor or detect the pressure on the support system 100 or on the patient. The pressure detecting system 250 may be configured and arranged to detect changes in pressure, stress, or strain, either directly or indirectly, that may be indicative of the amount of pressure being applied on the support system 100 or by the support system 100 on perianal tissue of the patient 10. For example, the pressure detecting system 250 may directly measure pressure using pressure sensors, or may indirectly measure pressure by monitoring, detecting, or responding to changes in shape, structure, or arrangement of various components or elements making up the support system 100.

In the exemplary embodiment shown in FIGS. 1-6, the pressure detecting system 250 comprises a plurality of strain gauges 252, 254 disposed on the perianal support member 102 and a user interface 256 (FIG. 6) in communication with the strain gauges 252, 254. In some embodiments, the strain gauges form a part of the perianal support member 102, while in other embodiments, they are adhered to the perianal support member 102. In the examples shown, a first strain gauge 252 is attached to the first compression element 116 and a second strain gauge 254 is attached to the second compression element 124. The strain gauges 252, 254 are arranged to detect strain in the compression elements 116, 124 in a manner indicative of loading applied to the external pressure surface at the anterior end 112 of the perianal support member and of loading at the posterior end of the perianal support member 104 as applied by the securing members 106, 107. The strain gauges 252, 254 may be any type of strain gauge including for example, a mechanical strain gauge, an electrical resistance strain gauge, an optical strain gauge, or other type of strain gauge.

FIG. 6 shows the strain gauges communicating with a user interface 256 that is configured to communicate information relating to the strain on the perianal support member 102 as detected by the strain gauges 252, 254, which is representative of pressure being applied by the perianal support member 102 to the patient. The user interface 256 may display or otherwise convey to a health care provider or the patient detected changes in pressure level, may display or otherwise indicate whether the pressure is within a suitable range, or may display or otherwise provide other feedback to the health care provider or patient indicative of pressure during the child delivery process. To do this, the user interface 256 communicates with the strain gauges 252, 254. Depending on the embodiment, the user interface 256 may communicate with the strain gauges 252, 254 either by wired connection or by a wireless connection. In some embodiments, signals from the strain gauges are processed by a processing system, and the user interface may receive information from the processing system indicative of information obtained by the strain gauges. In some embodiments, the user interface 256 is a table-top device that may be viewed by the health care provider or patient. In other embodiments, the user interface is a handheld structure, such a fob that may provide information to the health care provider or patient. Depending on the embodiment, the user interface may communicate detected information in any manner that may be understood by the health care provider or the patient. In one embodiment, the user interface 156 displays values from the strain gauges indicative of strain. In simpler embodiments, the user interface may display a red light when the absence of strain indicates that the perianal support system 100 is not applying a desired pressure to the perianal support device and a green light when the detected strain indicates that the perianal support system 100 is applying pressure within a desired range. Other interfaces are contemplated. When the strain gauges 252, 254 are of the type measuring electrical resistance though a conductor, the user interface 256 may also serve as a power source for the strain gauges. Other embodiments use strain gauges having an on-board power supply. Yet other arrangements are contemplated.

Some embodiments have a user interface 256 in the form of a smartphone or tablet, such as an iPhone®, an Android phone, an iPad®, or other similar device that is wirelessly connected with sensors 252 and 254. In this embodiment, the user interface 256 may operate a selectable application that may be downloaded to the user interface. In such embodiments, the patient or the healthcare provider may opt to view the information from the pressure detecting system on her own personal device. In some embodiments, the user interface 256 may display a graph with a line tracing the detected pressure as a timeline.

FIGS. 4-6 also show a migration barrier 194 that extends at least partially along the exterior side wall 150 of the first compression element 116 and at least partially along the exterior sidewall 160 of the second compression element 124. In some embodiments, the migration barrier may be formed of a soft, flexible silicon material configured to prevent the migration of fecal matter that may be expelled during childbirth. In this embodiment, the perianal support member may be located over the anus so that the migration barrier 194 is disposed between the anus and the vaginal opening. The migration barrier 192 may permit expelled matter to migrate only in the direction away from the vaginal opening. In the embodiment, shown, the migration barrier 194 extends at an oblique angle relative to the axis 152, 162 and may form a curved arc as can be seen by the hidden lines in FIG. 5. Other embodiments have a different angle and may be for example, purely linear or otherwise shaped.

FIG. 5 also shows an indicium 196 that helps a healthcare provider properly locate the perianal support member 102 on the patient. In this example, the indicium is a target shape formed on the perianal support member 102. In use, the health care provider may align the target with a body reference marker, such as the anus. This may help ensure the perianal support member 102 is properly located to support or treat perianal tissue while maintaining suitable spacing from the vaginal opening. Although a target shape is shown, other embodiments have other shapes or indicia as indicators. Indicia may find particular utility when using a transparent perianal support member 102. In this example, the indicium is spaced off-center from the axes 152, 162 in order to provide a suitable position of the perianal support member 102 on the patient.

Figure 7:
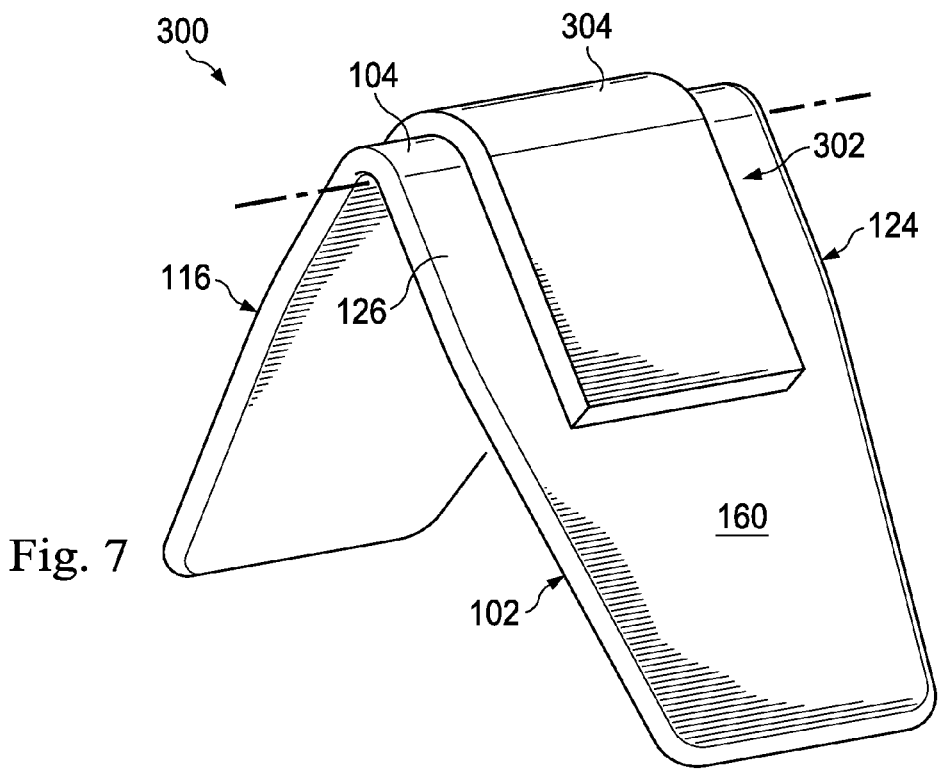
FIG. 7 is a perspective view of a portion of another perianal support system according to an exemplary embodiment.
Figure 8:
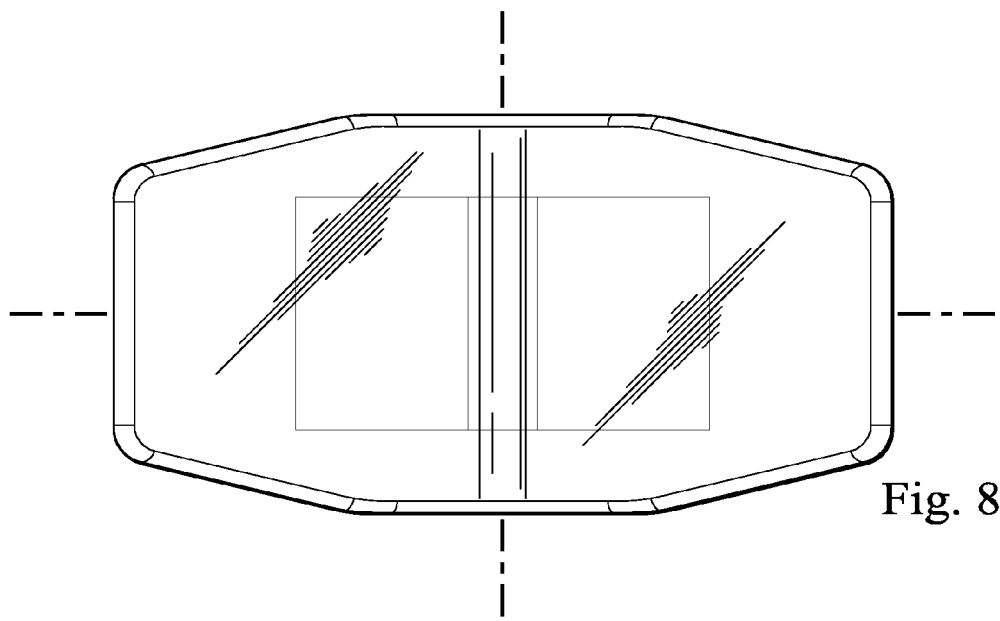
FIG. 8 is an end view of a portion of the perianal support system of FIG. 7.
Figure 9:
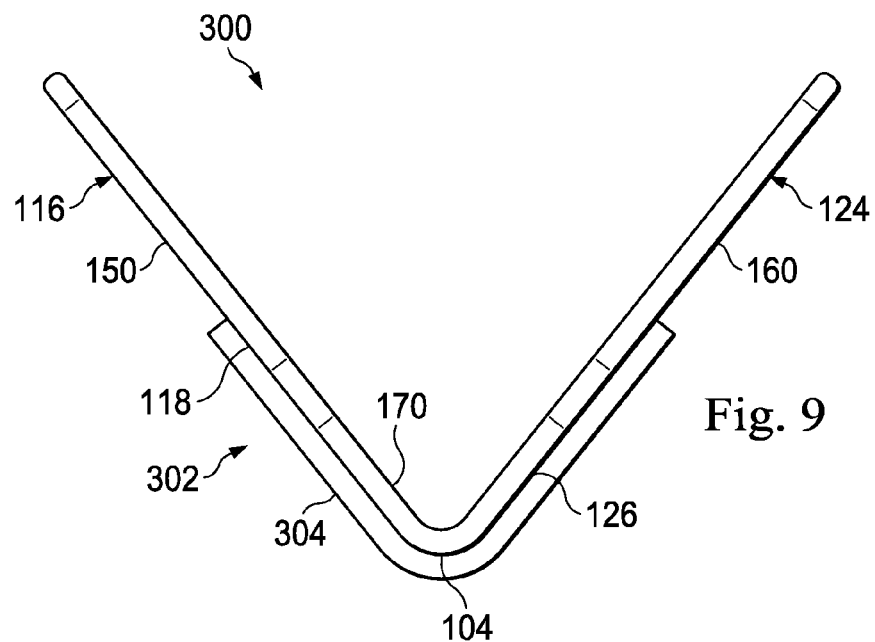
FIG. 9 is a side view of a portion of the perianal support system of FIG. 7.

FIGS. 7-9 show a portion of another exemplary embodiment of a perianal support system 300 in accordance with an exemplary aspect of the present disclosure. The support system 300 may include the perianal support member 102 and the securing members 106, 107 as described above with reference to the support system 100 in FIGS. 1-6. In this example, at least a portion of the perianal support member 102 may be formed of a material enabling passage of light through the perianal support member 102. In this embodiment, the light passing through the perianal support member 102 may be used as an indication of whether suitable pressure is being applied on the perianal tissue as explained below.

In this example, the support system 300 includes a pressure detecting system 302 that comprises a pressure detecting compliant pad 304 adhered to the perianal support member 102 across the majority of the pressure surface 104. In some embodiments, the pressure-detecting compliant pad 304 has a width the same width as the perianal support member 102, and in other embodiments, the pressure-detecting compliant pad 304 has a width less than the width of the perianal support member 102. In the embodiment shown the pressure-detecting compliant pad 304 extends about the pressure surface 104 and extends at least partially along the exterior side wall 150 of the first compression element 116 and at least partially along the exterior sidewall 160 of the second compression element 124. The pressure detecting compliant pad 304 may be disposed and arranged as an interfacing structure disposed between the pressure surface 104 of the perianal support member and a patient's perianal tissue when the perianal support system 300 is disposed on a patient. As illustrated, a first portion of the complaint pad 304 extends along and is adhered to distal end portion 118 of the compression element 116. In a similar manner, a second portion extends along and is adhered to distal end portion 126 of the compression element 124. In one embodiment, the compliant pad 304 is a sterile gauze pad. In another embodiment, the compliant pad 304 includes an internal cushioning structure, such as polyurethane, silicon, rubber, foam, cotton, etc., with a non-abrasive skin contact surface. The compliant pad 304 may be adhered to the perianal support member 102 across the majority of the pressure surface 104. In one embodiment, the compliant pad is die cut from 1776 and 1772 stock materials from 3M. Then bonding the resulting laminate on to the compression surface as the 1772 material has an adhesive back. In another embodiment, compliant pad 304 is an absorbent material adapted to absorb bodily fluids. It will be appreciated that the compliant pad 304 may make placement and maintenance of the support device 300 more comfortable for the patient. In addition, the surface of the pad 304 is configured to frictionally engage the patient's perianal tissue to inhibit movement between the support device 300, particularly the pressure surface 104 and the patient. In still a further aspect, compliant pad 304 includes a treating compound. The treating compound is disposed within the pad, applied on the surface, or a combination of both. Treating compounds useful for combination with pad 304 include, but without limitation to other compounds, antibacterial compounds, antibiotic compounds, sclerants, antimicrobial compounds, anti-inflammatory compounds, anti-fungal agents, anti-itching agents, humicants, moisture absorbing agents, gas absorbing agents, buffering agents for pH control, drying agents and the like and coagulants. In yet a further embodiment, pad 304 is not fixed to the perianal support member 102 but is instead positioned on the patient in advance of positioning the perianal support member 102 or is loosely held to the perianal support member 102 as it is applied to the body. In this embodiment, perianal support member 102 maintains the position of the pad 304 relative to the patient's body and in particular the anal orifice.

In one embodiment, the compliant pad 304 is a flexible fabric pressure sensor formed of an outer layer arranged to interface with and apply pressure to the perianal tissue of the patient, a stretch conductive fabric, an Ex-static® fabric, a non-conductive adhesive, an energy source, a light source, and connection cables. A microcontroller may translate sensor values into the output values into a signal indicative of pressure.

In an alternative embodiment, the pressure detecting compliant pad 304 may be designed to change colors when pressure on the pad exceeds a threshold pressure. The threshold pressure may be preset and may be established to correspond with a therapeutic pressure that is considered suitable to support the perianal tissue of the patient during the child delivery process. In one exemplary embodiment, the pad 304 is a Mylar based film that contains a layer of tiny microcapsules. The application of force upon the pad causes the microcapsules to rupture, producing an instantaneous and permanent high resolution "topographical" image of pressure across the contact area. A film having such a construction is marketed under the trade name FujiFilm Prescale®. Some compliant pad embodiments include a liquid gel covering a colored backing. Under pressure, the gel displaces revealing the colored backing, and indicating to the health care provider that a pressure threshold has been met. Other types of color indicators are also contemplated.

Some embodiments of the pressure detecting compliant pad are configured to dynamically display the color from a low intensity color to a higher intensity color indicative of the amount of pressure. Such pads showing a graduated scale may also indicate when the pressure exceeds therapeutic pressure. When such instances occur, the healthcare provider may adjust the perianal support member 102 to reduce the pressure on the perianal tissue. In some embodiments, the pressure detecting compliant pad 304 operates as a pressure switch, where the pad 304 is a first color when the switch is off, and where the pad changes color when the switch is on.

Since the perianal support member 102 allows passage of at least some visible light, a health care provider may be able to visually determine when a therapeutic pressure is applied on the pressure-detecting compliant pad 304 based on the color emitted from the pressure detecting compliant pad 304. In some aspects, the health care provider, even when positioned to receive a baby during delivery, can visually observe at least some light emitted from the pressure-detecting compliant pad 304 be observing through the internal contact surface 170 in the access cavity 136 of the perianal support member 102. In some embodiments, the perianal support member 102 is formed of a clear plastic material that enables a health care provider to directly see the pressure detecting compliant pad 304. Some clear plastic materials may include acrylics or other types of polymer materials. Other embodiments are only partially transparent and may permit passage of light through the perianal support member 102 so that a health care provider can visually observe the color of the pressure-detecting compliant pad. A partially transparent perianal support member may visually cover the patient tissue under pressure but may still permit the changes in color to be recognized by the health care provider.

In some embodiments, the pressure detecting compliant pad 304 may include a power source that provides power to electronics for emitting a light or for causing the pressure detecting compliant pad 304 to emit light of a particular color. Other embodiments undergo a chemical reaction or other transformation when the threshold pressure level is exceeded. The reaction or transformation causes the color change in the pressure detecting compliant pad 304.

Figure 10:
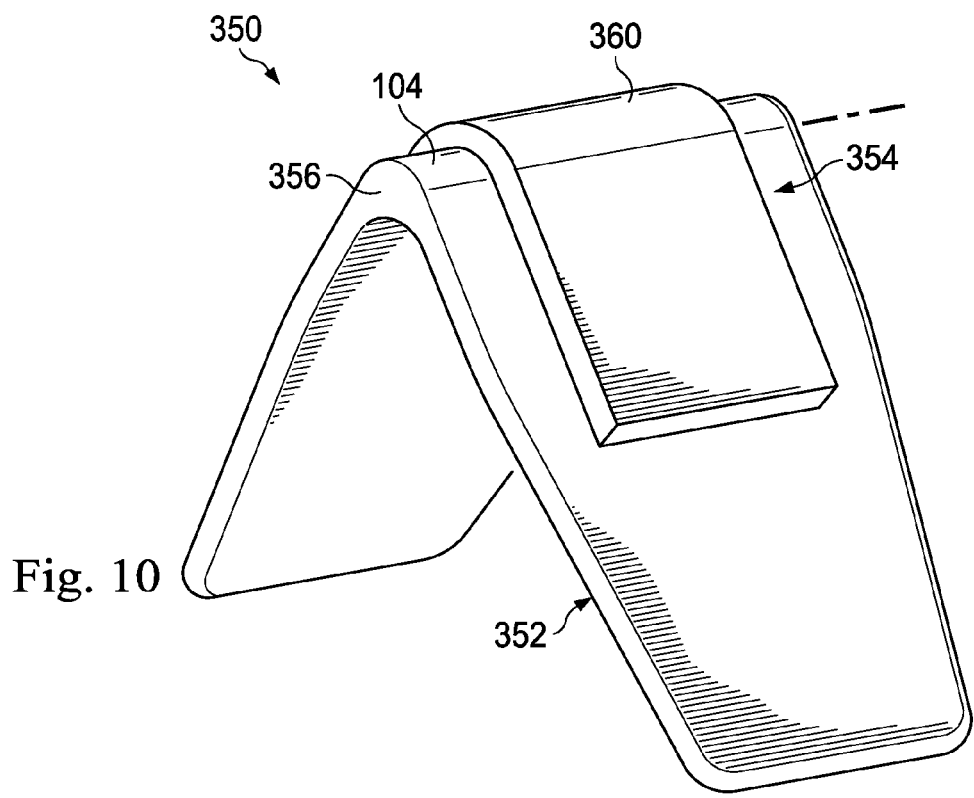
FIG. 10 is a perspective view of a portion of another perianal support system according to an exemplary embodiment.
Figure 11:
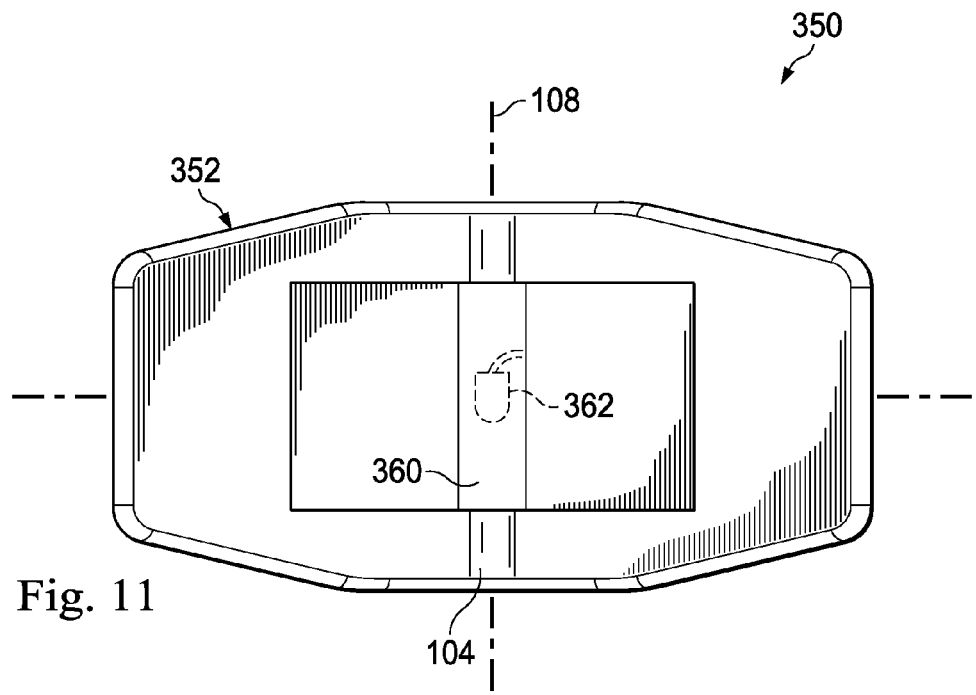
FIG. 11 is an end view of a portion of the perianal support system of FIG. 10.
Figure 12:
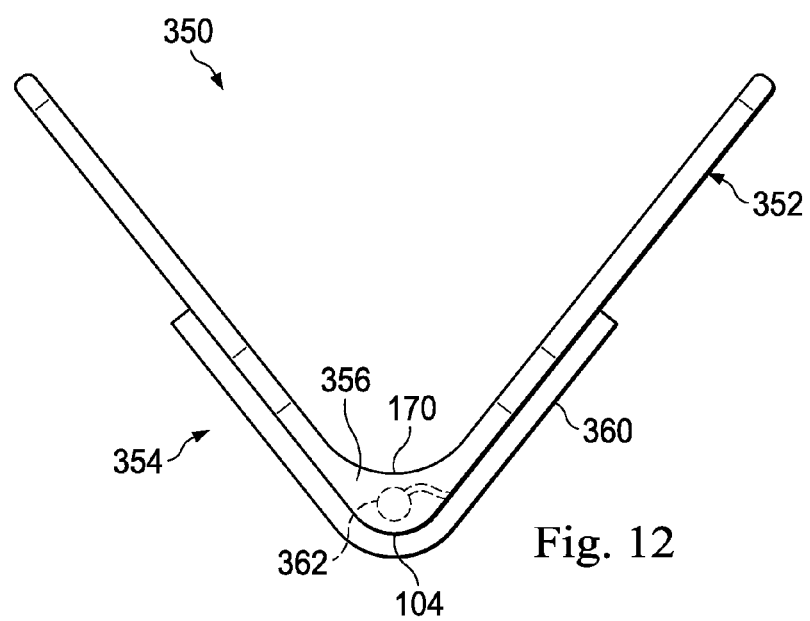
FIG. 12 is a side view of a portion of the perianal support system of FIG. 10.

FIGS. 10-12 show a portion of another exemplary embodiment of a perianal support system 350 in accordance with an exemplary aspect of the present disclosure. This exemplary embodiment includes a pressure detecting compliant pad as discussed above, however the pad operates as a switch associated with an LED indicator. When the desired or the therapeutic pressure is reached on the pressure detecting compliant pad, the bulb may be turned on as an indicator to indicate to the health care provider that the threshold therapeutic pressure has been met. The support system 350 disclosed herein includes a perianal support member 352 and a pressure detecting system 354. The pressure detecting system includes a pressure detecting compliant pad 360 and an LED bulb 362. These are discussed further below. The perianal support member 352 has many of the same features and shape as the perianal support member 102 discussed above. Therefore a description of the entire perianal support member 352 will not be repeated here recognizing that the description above applies to the perianal support member 352. However, in this embodiment, the perianal support member 352 includes a thick pressure zone 356 disposed between the external pressure surface 104 and the internal contact surface 170. The thick pressure zone 356 is configured to house a portion of the pressure detecting system 354. In this embodiment, the thick pressure zone 356 has a thickness greater than the thickness of the LED bulb 362, and fully encompasses the LED bulb 362. Because of its shape, the perianal support member 352 includes an external pressure surface 104 similar to that discussed above, and the internal contact surface 170 has a curved surface that is not concentric with the external pressure surface 104. In some embodiments, the internal contact surface 170 is a planar surface extending between the first and second compression elements. In use, a health care provider can manually provide pressure on the internal contact surface 170 to hold the perianal support member 352 in place on the patient until the first and second securing members are properly positioned. The thick pressure zone 356 fully encompasses the LED bulb 362 and protects the LED bulb 362 from damage that might otherwise occur when the health care provider applies pressure on the internal contact surface 170.

The pressure detecting compliant pad 360 in this embodiment is responsive to changes in pressure and may be a pressure switch responsive at a repeatable and preset pressure. In some embodiments, a pressure detecting compliant pad 360 may be formed of an outer layer arranged to interface with and apply pressure to the perianal tissue of the patient, a stretch conductive fabric, an Ex-static® fabric, a non-conductive adhesive, an energy source, a light source, and connection cables. A microcontroller may translate detected pressure into output signals indicative of the detected pressure.

The LED bulb 362 may form a part of a circuit with the pressure detecting compliant pad 360 and may be in electrical communication with the pressure detecting compliant pad 360. A power source (not shown) may also be disposed adjacent the LED bulb 362 in the thick pressure zone 356 of the perianal support member 352. Although LED's are provided for the purpose of illustration, the type of visual indicator is not limited to LED's and other light sources or visual indicators can be utilized with the present disclosure.

In some embodiments, the LED bulb 362 is a multi-colored LED bulb with each color indicative of a separate pressure threshold. In one exemplary embodiment, no light may indicate pressure below a minimum threshold and the LED bulb 362 may display green after exceeding a first pressure threshold. The green zone of pressure may provide static support pressure indication capability which may correspond to a pressure range that provides therapeutic support in a relatively static condition. During contractions and after exceeding a second pressure threshold, the LED may change to yellow indicating an increase in pressure. This yellow zone may provide dynamic support pressure indication capability, which may suggest that the patient is effectively pushing the baby toward the vaginal opening during the contraction. The yellow light is intended to provide dynamic feedback during the dynamic stages of a contraction. In still an alternative feature, if a third pressure threshold is exceeded, the LED may change to red to indicate an unsafe pressure range. This red zone may provide extreme support pressure indication capability indicating that pressure on the perianal tissue should be reduced. Therefore, this condition alerts the user to either cease the pushing contractions or reposition or remove the perianal support device. The first, second, and third pressure thresholds may be selected to correspond to desired therapeutic pressures. For example, the LED bulb 362 may shine with a green light when the first pressure threshold is exceeded indicating that a partially effective pressure is being applied to the perianal tissue, and may shine with a yellow light when the second pressure threshold is exceeded indicating that more effective pressure is being applied to the perianal tissue.

In another embodiment, the LED bulb 362 is not embedded in a thick pressure zone, but is disposed on the perianal support member 352 in a manner that the LED bulb may be monitored by the health care provider. In this embodiment, pressure on the compliant pad 360 may switch on the LED bulb 362 which may be disposed anywhere along the perianal support member 352. In such embodiments, the transparency of the perianal support member 352 does not impact the effectiveness of the pressure detecting system 354.

Figure 13:
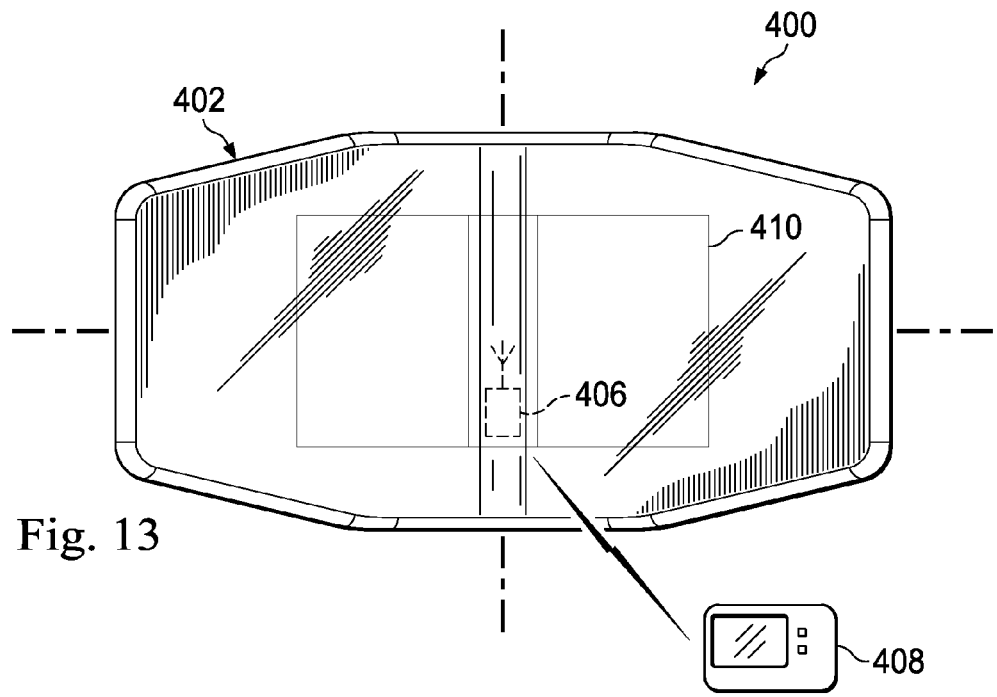
FIG. 13 is an end view of a portion of another perianal support system according to an exemplary embodiment.
Figure 14:
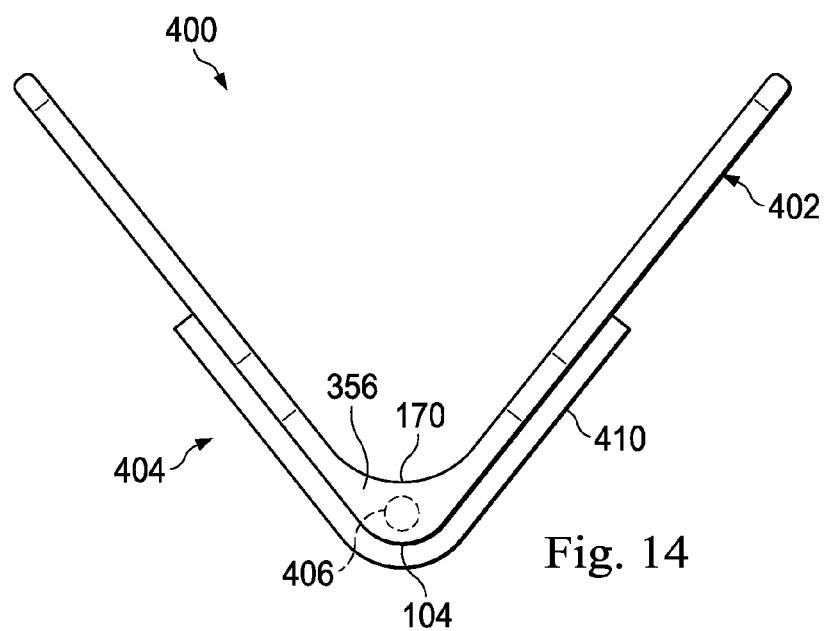
FIG. 14 is a side view of a portion of the perianal support system of FIG. 3.

FIGS. 13 and 14 show a portion of another exemplary embodiment of a perianal support system 400 in accordance with an exemplary aspect of the present disclosure. This exemplary embodiment includes a perianal support member 402 and a pressure detecting system 404 that includes a transmitter 106 and an off-board receiver 408. In this embodiment, the perianal support member 402 is shaped in the same manner discussed above with reference to FIGS. 10-12 and includes a thick pressure zone 356 at the apex between the external pressure surface 104 and the internal contact surface 170. In this embodiment however, the pressure detecting system 404 includes a transmitter 406, a receiver 408, and a pressure detecting compliant pad 410. The transmitter 406 is disposed on the perianal support member 402 in addition to or in place of the LED bulb 362 shown in FIGS. 11 and 12. The transmitter 406 is in communication with the pressure detecting compliant pad 410 and may be configured to receive signals indicative of pressure detected by the pressure detecting compliant pad 410. In some embodiments, the signals may have been processed by a microcontroller carried on or otherwise in communication with the pressure detecting compliant pad 410. In some embodiments, the signals may be directly transmitted signals representative of pressures detected by the pressure detecting compliant pad 410. In other embodiments where the pressure detecting compliant pad 410 is a pressure switch, the signals may be an on/off signal indicative of an open or closed circuit.

Depending on the embodiment, the transmitter 406 may communicate using any uni-directional or bi-directional radio communication format. Different embodiments include, for example, a Wi-Fi bi-direction radio communication capability and a Bluetooth bi-direction radio communication capability that allow wireless communication following the Wi-Fi Alliance standard and Bluetooth Special Interest Group standard. Of course, other wireless local area network (WLAN) standards and wireless personal area networks (WPAN) standards can be used.

The transmitter 406 transmits signals from the perianal support member 402 to the off-board receiver 408. The receiver 408 may comprise an antenna, and receiver circuitry for processing the signals received from the transmitter 406. Depending on the embodiment, the receiver 108 may include a microprocessor configured to interpret the signals and output information via a user interface to a health care provider or the patient. In one embodiment, the processor is configured to output actual pressure values acting on the pressure detecting compliant pad 410. In other embodiments, the microprocessor is configured to output information indicating to the health care provider whether more pressure or less pressure is recommended in order to reduce the incidence of perianal tissue damage. In one embodiment, the receiver 408 is configured with a simple user interface that indicates whether the applied pressure is above or below a therapeutic pressure threshold. In this embodiment, the user interface may be a single bulb that turns on when the signal from the transmitter indicates that the therapeutic pressure threshold has been reached.

Although disclosed as being used with the pressure detecting compliant pad 410, the transmitter 406 and receiver 408 may be used with any pressure sensing system disclosed herein, including the strain gauges, the visual indicator pad, the LED indicator, as well as the others. The off-board receiver 408 may store and record information obtained. In one example, the information is displayed over time.

When the receiver 408 is in the form of a smartphone or tablet, such as an iPhone®, an android phone, an iPad®, or other similar device as discussed above, the receiver may process and display the information received from the transmitter on a screen. In some embodiments, the receiver 408 communicates with the transmitter via blue-tooth, while in other embodiments, the communications occur over a Wi-Fi network.

As discussed above with reference to FIGS. 1-3, the perianal support system 100 includes the first and second securing members 106, 107. FIGS. 15-28 show different securing members that may secure the perianal support member against the perianal tissue of the patient. Depending on the embodiment, the securing members may attach to the patient, such as the patient's flanks, or may extend between the perianal support member and anchor pads. Other securing members extend between the perianal support member and the patient or inanimate objects, such as a part of the delivery bed. The securing members disclosed herein may be configured and arranged to provide an indication, such as a visual indication for example, of the load being applied on the perianal tissue by the perianal support member. In some embodiments, the securing members are arranged to indicate when a suitable therapeutic load is applied to the perianal tissue based on the tension applied to the securing members.

Figure 15:
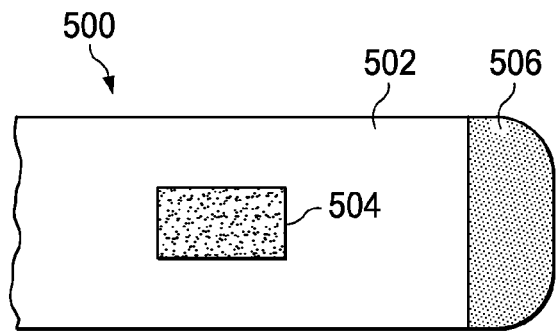
FIG. 15 is a view of a portion of another perianal support system according to an exemplary embodiment in an unstretched condition.
Figure 16:
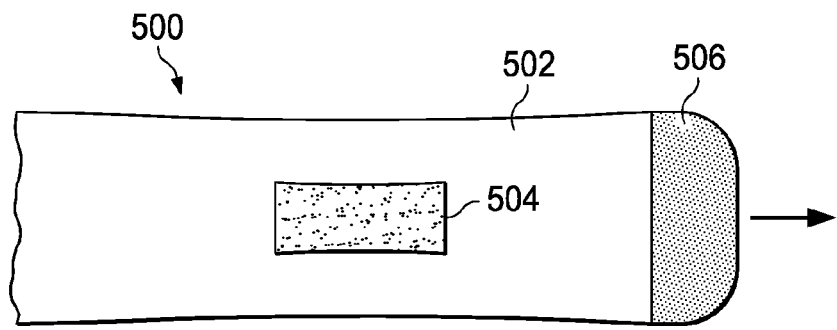
FIG. 16 is a view of the portion of the perianal support system of FIG. 15 in a stretched condition.

FIGS. 15 and 16 shows an exemplary pressure detecting system 500 comprising a securing member 502 that may be employed to secure the perianal support member 102 in place of the securing member 106 or 107 discussed above. Here, the pressure detecting system 500 also includes a pressure detecting portion 504. Some embodiments employ two securing members, and each securing member may include the same features. In other embodiments, only one securing member forms the pressure detecting system 500, and the other securing member does not form the pressure detecting system 500 as it may not provide feedback to the health care provider or patient.

The securing member 502 may be formed of a substantially elastically extending or substantially non-extending strap. In this embodiment, it includes a connection portion 506 to which a portion of a hook and loop fastener may be adhered. The hook and loop fastener may enable the securing member 502 to be adhered in place to a corresponding hook and loop fastener, such as an anchor pad. A health care provider can stretch the securing member 502 to the increase or decrease the load applied on perianal tissue by the perianal support member.

The pressure detecting portion 504 in this embodiment is a tension detecting pad. The tension detecting pad is arranged to detect strain during the loading process and provide information to a user indicative of the amount of loading on the securing member 502. In one embodiment, it does this by changing colors, thereby providing a visual indicator to the health care provider or patient of the amount of loading on the securing member 502. The amount of strain on the securing member 502 may be directly correlated with the amount of pressure on the perianal tissue. In one embodiment, the pressure detecting portion 504 changes color depending on the amount of strain or stretch. The amount of stretch is directly correlated with the loading on the perianal support member, and therefore, the color displayed by the pressure detecting portion 504 is directly correlated with loading on the perianal support member. In one example the pressure detecting portion 504 is a neutral color when in an unloaded or a neutral condition, and changes to a green color when the tension in the securing member 502 is sufficient to provide a desired load on the perianal tissue by the perianal support member. In some embodiments, the color changing abruptly occurs when a strain that applies a therapeutic pressure is reached, and in other embodiments, the color change is graduated so that a health care provider or the patient can determine about what loading is being applied at any one time. Accordingly, the securing member 502 may be applied to a patient in an initial static support position. Color changes during contractions indicate higher pressures. As such, the device may provide positive user feedback on dynamic pressure changes indicative of the success or lack thereof of pushing associated with contractions. It's worth noting that the perianal support system may be retained in position both during the static support phase and the dynamic support phase of the birthing process.

In some embodiments, the securing member 502 is formed of an elastically extending strap with elastomeric properties enabling the securing member 502 to stretch from a neutral condition when no load is applied to a stretched condition, when the securing member 502 is under a tension load. In such an embodiment, the strain or the stretch under load may be much greater than in other embodiments where the securing member 502 formed of a substantially non-elastic material. In such embodiments, the securing member 502 has elastic spring properties, such that the greater the distance of the stretch, the greater the load required. Other embodiments have a substantially non-elastic securing member 502. Accordingly, the amount of strain is much less under load. The color changing indicator pad may be arranged to correspond with a particular securing member property type in order to provide a repeatable indicator to the health care provider or patient. In some embodiments, the securing member 502 is formed of a thin-napped Lycra material.

FIG. 15 shows the securing member 502 and the pressure detecting portion 504. In FIG. 15, the securing member is under a first load or is under no load. Therefore, the pressure detecting portion is a first color. In FIG. 16, the pressure detecting securing member 502 is under a second, greater load, and has introduced an increased level of strain into the securing member 504. As can be seen, the color is pad is also lengthened and as a result, displays a different color. While shown as making up only a portion of the securing member 502, in some embodiments, the pressure detecting portion 504 has the same width and/or length as the securing member 502 and in some embodiments, the pressure detecting portion 504 makes up the entire securing member 502.

Figure 17:
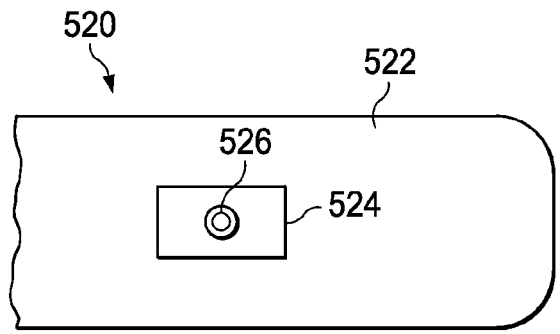
FIG. 17 is a view of a portion of another perianal support system according to an exemplary embodiment in an unstretched condition.
Figure 18:
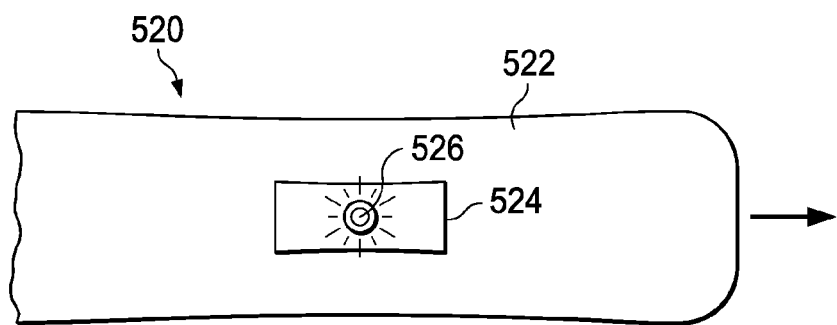
FIG. 18 is a view of the portion of the perianal support system of FIG. 17 in a stretched condition.

FIGS. 17 and 18 show another embodiment of an exemplary pressure detecting system 520 comprising a securing member 522 that may be employed to secure the perianal support member 102 in place of the securing member 106 or 107 discussed above. Here, the pressure detecting system 520 also includes a pressure detecting portion 524 that may provide information to the health care provider or patient that a sufficient tension is reached to apply a desired load through the perianal support member 102 onto the perianal tissue. This embodiment is similar in many respects to the pressure detecting system 500 discussed above. However, this embodiment includes an electrical light indicator 526 in place of the color changing indicator tension detecting pad discussed above. In this embodiment, the strain or change in length of the strap can be monitored and used to provide feedback to the light indicator 526. The light indicator 526 is, in the embodiment shown, an LED bulb that is configured to emit light when powered. Leads on the LED connect to a power source and to a strain detector that may operate as a switch when the strain exceeds a threshold strain. The threshold strain may be selected to correspond to a desired pressure on the perianal tissue when the securing member 522 is angled to provide the loading through the perianal support member. In one embodiment, the angle is one shown in FIG. 1, where the securing member extends to the lateral flanks.

FIG. 17 shows the securing member 522 and the pressure detecting portion 524. In FIG. 17, the securing member 522 is under a first load or is under no load. Therefore, the pressure detecting portion 524 is off, or is not lit. In FIG. 15, the pressure detecting securing member 522 is under a second, greater load, and has introduced a sufficient level of strain into the securing member 522. As can be seen, the pressure detecting portion 524 is therefore on, powered, or lit, indicating that the securing member 522 is under a tension load sufficient to apply suitable tension on the perianal tissue.

Figure 19:
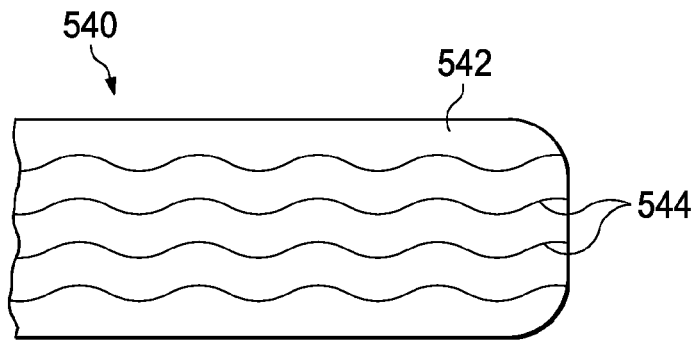
FIG. 19 is a view of a portion of another perianal support system according to an exemplary embodiment in an unstretched condition.
Figure 20:
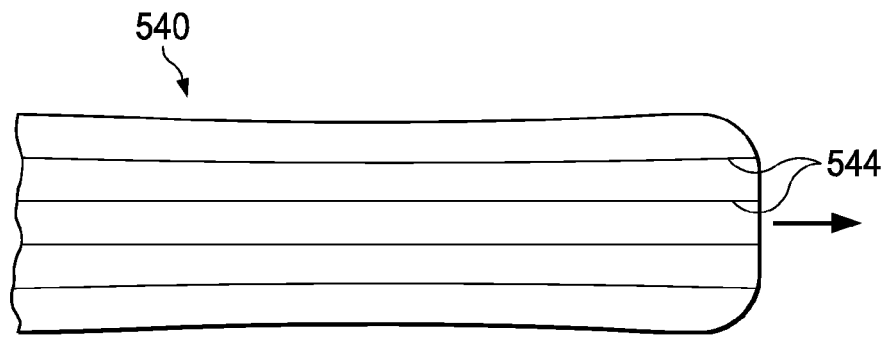
FIG. 20 is a view of the portion of the perianal support system of FIG. 19 in a stretched condition.

FIGS. 19 and 20 show another embodiment of an exemplary pressure detecting system 540 comprising a securing member 542 that may be employed to secure the perianal support member 102 in place of the securing member 106 or 107 discussed above. Here, the pressure detecting system 540 also includes a pressure detecting portion 544 that may provide information to the health care provider or patient that a sufficient tension is reached to apply a desired load through the perianal support member 102 onto the perianal tissue. In this embodiment, the securing member 542 is an elastically extending member that may extend from a neutral or un-stretched condition to a stretched condition. In some embodiments, the securing member 542 has elastic properties where the tension force increases non-linearly as the material is stretched.

The pressure detecting portion 544 in this embodiment comprises a plurality if inelastic fibers or indicators whose profiles provide an indication of tension loading on the pressure detecting system 540. The pressure detecting portion 544 can be seen in both FIGS. 19 and 20. In FIG. 19, the inelastic fibers are curved or are not straight. This may indicate that the tension loading on the securing member 542 is less than a threshold pressure, and therefore, the securing member 542 is not providing a desired load on the perianal tissue through the perianal support member. FIG. 20 shows the securing member 542 stretched further than in FIG. 19. As a result, the inelastic fibers have straightened out. In this embodiment, the securing member and the pressure detecting portion 544 is designed so that the desired pressure on the perianal tissue corresponds with the straightening of the inelastic fibers. Accordingly, when the inelastic fibers are substantially straight, the pressure on the perianal tissue has reached or exceeded the desired loading on the perianal tissue. The fiber profile in FIG. 20 corresponds to a desired pressure on the perianal tissue.

Figure 21:
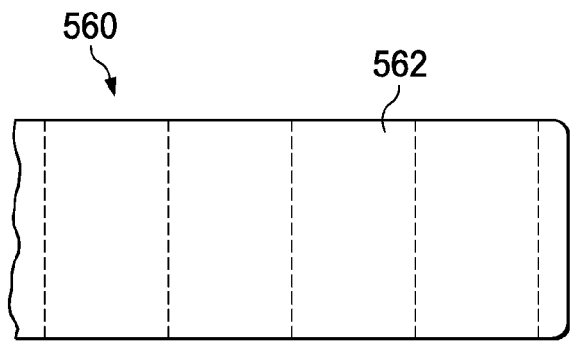
FIG. 21 is a view of a portion of another perianal support system according to an exemplary embodiment in an unstretched condition.
Figure 22:
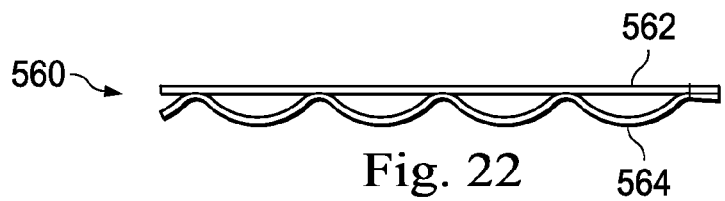
FIG. 22 is a side view of the portion of the perianal support system of FIG. 21.
Figure 23:
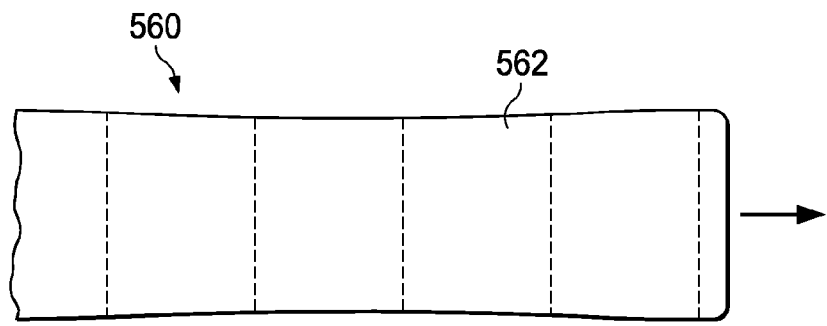
FIG. 23 is a view of the portion of the perianal support system of FIG. 21 in a stretched condition.
Figure 24:
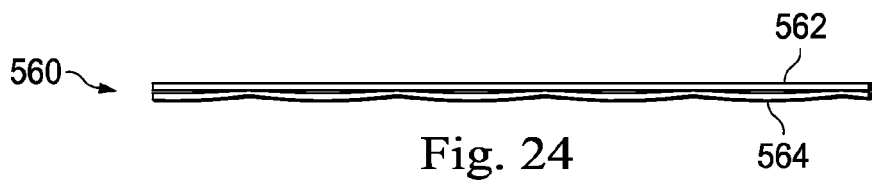
FIG. 24 is a side view of the portion of the perianal support system of FIG. 21 in a stretched condition.

FIGS. 21-24 show yet another embodiment of an exemplary pressure detecting system 560 comprising a securing member 562 that may be employed to secure the perianal support member 102 in place of the securing member 106 or 107 discussed above. FIGS. 21 and 22 show the pressure detecting system 560 in an un-stretched state and FIGS. 23 and 24 show the pressure detecting system 560 in a stretched state. FIGS. 21 and 23 show a top view of the pressure detecting system 560 and FIGS. 22 and 24 show side views. Here, the pressure detecting system 560 also includes a pressure detecting portion 564 that may provide information to the health care provider or patient that a sufficient tension is reached to apply a desired load through the perianal support member 102 onto the perianal tissue. In this embodiment, the securing member 562 is an elastically extending member that may extend from a neutral or un-stretched condition to a stretched condition as discussed above.

The pressure detecting portion 564 is in this embodiment comprises an inelastic strap or indicator whose profile provides an indication of tension loading on the pressure detecting system 560. The pressure detecting portion 564 can be seen best in FIGS. 21 and 23. In FIGS. 19 and 20, the inelastic strap is not stretched or is not taut. This may indicate that the tension loading on the securing member 562 is less than a threshold pressure, and therefore, the securing member 562 is not providing a desired load on the perianal tissue through the perianal support member. FIGS. 21 and 22 show the securing member 542 stretched further than in FIGS. 19 and 20. As a result, the inelastic strap has straightened out. In this embodiment, the securing member 562 and the pressure detecting portion 564 are designed so that the desired pressure on the perianal tissue corresponds with the straightening of the inelastic strap. Accordingly, when the inelastic strap is substantially straight, the pressure on the perianal tissue has reached or exceeded the desired loading on the perianal tissue.

Figure 25:
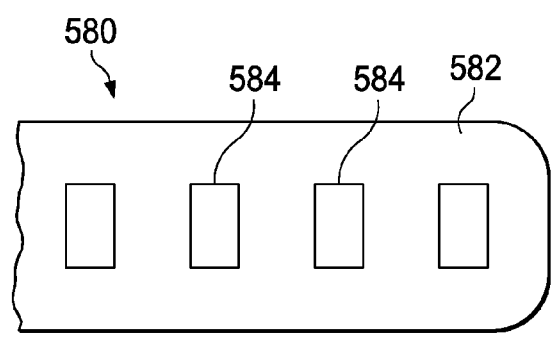
FIG. 25 is a view of a portion of another perianal support system according to an exemplary embodiment in an unstretched condition.
Figure 26:
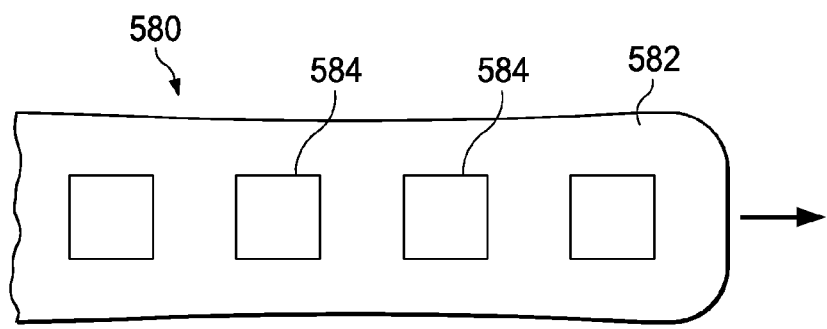
FIG. 26 is a view of the portion of the perianal support system of FIG. 26 in a stretched condition.

FIGS. 25 and 26 show another embodiment of an exemplary pressure detecting system 580 comprising a securing member 582 that may be employed to secure the perianal support member 102 in place of the securing member 106 or 107 discussed above. FIG. 25 shows the pressure detecting system 580 in an un-stretched state and FIG. 26 shows the pressure detecting system 580 in a stretched state. Here, the pressure detecting system 580 also includes a pressure detecting portion 584 that may provide information to the health care provider or patient that a sufficient tension is reached to apply a desired load through the perianal support member 102 onto the perianal tissue. In this embodiment, the securing member 582 is an elastically extending member that may extend from a neutral or un-stretched condition to a stretched condition as discussed above.

The pressure detecting portion 584 in this embodiment comprises a reference shape or indicator formed in the elastic strap whose profile provides an indication of tension loading on the pressure detecting system 580. The pressure detecting portion 584 is shown in FIG. 25 having a series of non-square rectangular shapes in an un-stretched state. This may indicate that the tension loading on the securing member 562 is less than a threshold pressure, and therefore, the securing member 562 is not providing a desired load on the perianal tissue through the perianal support member. As the securing member 582 is stretched, the shape of series of non-square rectangular shaped changes to a square shape. This may indicate that a desired tension is in the securing member 582 sufficient to apply a desired load on the perianal tissue through the perianal support member 102 when the securing member is applied in a particular location, such as along the lateral flanks of the patient.

The securing member 582 and the pressure detecting portion 584 are designed so that the desired pressure on the perianal tissue is achieved when the shape of the pressure detecting portion 584 becomes square. Accordingly, when the shape of the pressure detecting portion 584 is substantially square, the pressure on the perianal tissue has reached or exceeded the desired loading on the perianal tissue. While the shape is shown as square in the embodiment shown, other shapes are contemplated including, for example, any geometric figure, such as circles, stars, and so on. The shapes may be imprinted at intervals or woven or otherwise incorporated into the fabric of the securing member 582.

Figure 27:
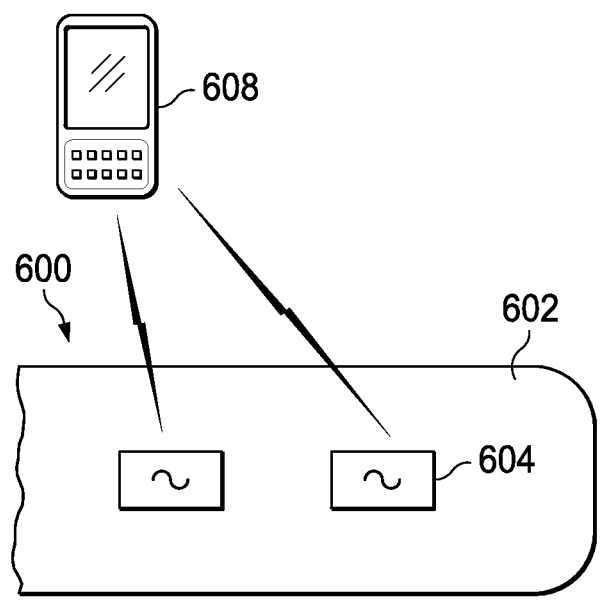
FIG. 27 is a view of a portion of another perianal support system according to an exemplary embodiment in an unstretched condition.
Figure 28:
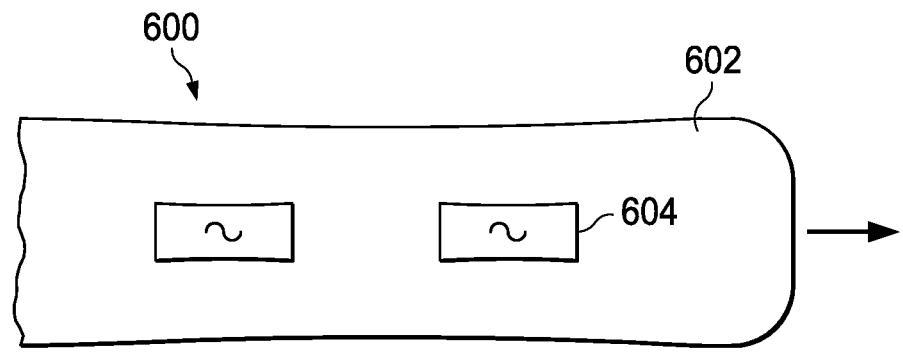
FIG. 28 is a view of the portion of the perianal support system of FIG. 17 in a stretched condition.

FIGS. 27 and 28 show another embodiment of an exemplary pressure detecting system 600 comprising a securing member 602 that may be employed to secure the perianal support member 102 in place of the securing member 106 or 107 discussed above. FIG. 27 shows the pressure detecting system 600 in an un-stretched state and FIG. 58 shows the pressure detecting system 600 in a stretched state. Here, the pressure detecting system 600 also includes a pressure detecting portion 604 that may provide information to the health care provider or patient that a sufficient tension is reached to apply a desired load through the perianal support member 102 onto the perianal tissue. In this embodiment, the securing member 602 is an elastically extending member that may extend from a neutral or un-stretched condition to a stretched condition as discussed above, and the pressure detecting portion 602 is one or more strain gauges that measure the strain or extension of the securing member 602 in the manner discussed above. In this embodiment, each strain gauge is associated with a wireless transmitter that transmits the detected information to an off-board interface device 608 that may communicate information to the health care provide or the patient. The off-board interface device 608 and the transmitter may work in a manner similar to those discussed above and may display either information related to the real-time pressure or may display threshold information indicating whether the pressure is above or below the threshold.

The pressure detecting portions disclosed herein may enable a health care provider of the patient to apply the perianal support device with at least a proper amount of pressure to provide therapeutic support to the patient during childbirth. Accordingly, the perianal device may reduce the incidence of a number of complications, including for example and without limitation, pelvic floor incompetence or dysfunction, organ prolapse, incontinence secondary to pressure and stretching exerted on bladder and bladder neck, over stretching, perineum tears and lacerations, forceps use, and hemorrhoids.

In some embodiments, the perianal support systems describe herein are configured to count uterine contractions by monitoring the pressure changes invoked on the perianal support member 102 by the perianal tissue. That is, during contractions, the perianal support systems described herein may be configured to detect a change in pressure that occurs due to muscle displacement of the perianal tissue. During labor, the contractions of the uterus, along with movement of the baby's head as a result of the uterine muscles, physically displace the perianal tissue. When the perianal tissue is supported by the perianal support systems described herein, the result is less perianal tissue displacement and an increase in net pressure against the external pressure surface 104 of the perianal support member 102. These increases in pressure against the pressure surface 104 can be detected using the pressure detecting systems described above. Accordingly, in addition to measuring the pressure statically upon application of the perianal support device, the system may be used to monitor dynamic pressure by detecting changes in pressure at the perianal tissue resulting from uterine contractions.

Any of the embodiments described herein may also be used to mechanically or electrically count uterine contractions by monitoring the changes in pressure that occur during each contraction. An exemplary mechanical counter includes for example, a spring loaded plunger that may displace with displacement of perianal tissue. The plunger may drive a cog or gear to rotate a counting mechanism in a manner similar to hand-held mechanical counters that count the times a plunger is pressed. The counter may display a number disposed for viewing on a numbered wheel indicative of the number of times the plunger presses or the tissue displaces. Some embodiments employ the user interfaces described above to count each time that the pressure changes by a pre-programmed amount. For example, the pressure detection system may store count each time the pressure increases by a pre-set amount or each time the pressure exceeds a threshold level. In addition to counting the contractions, the system may also determine the time between contractions. Depending on the embodiment, this information may be stored and displayed to a user using any of the interfaces disclosed herein. In some embodiments, the pressure may be shown in real-time as a graph on the user interface devices. Pressure peaks may indicate the start of a contraction, and the time period between peaks may be indicative of the time between contractions.

Any of the embodiments described herein may also make up a push meter configured to provide an indication of the strength of a push during the birthing process. For example, by monitoring the changes in pressure on the perianal tissue by the support member 102 that occur during a push, the pressure detection systems may be able to provide a pressure indication of the strength of a push. In some embodiments, the strength of the push may be displayed on a user interface in a graph form on a user interface. In other embodiments, the strength of the push may be indicated by the color change, the light bulb activation or other indicator described herein or that might otherwise indicate the strength of a push. Accordingly, during the birthing process, the patient and/or the healthcare provider may observe the systems to determine the strength of a push.

Figure 29:
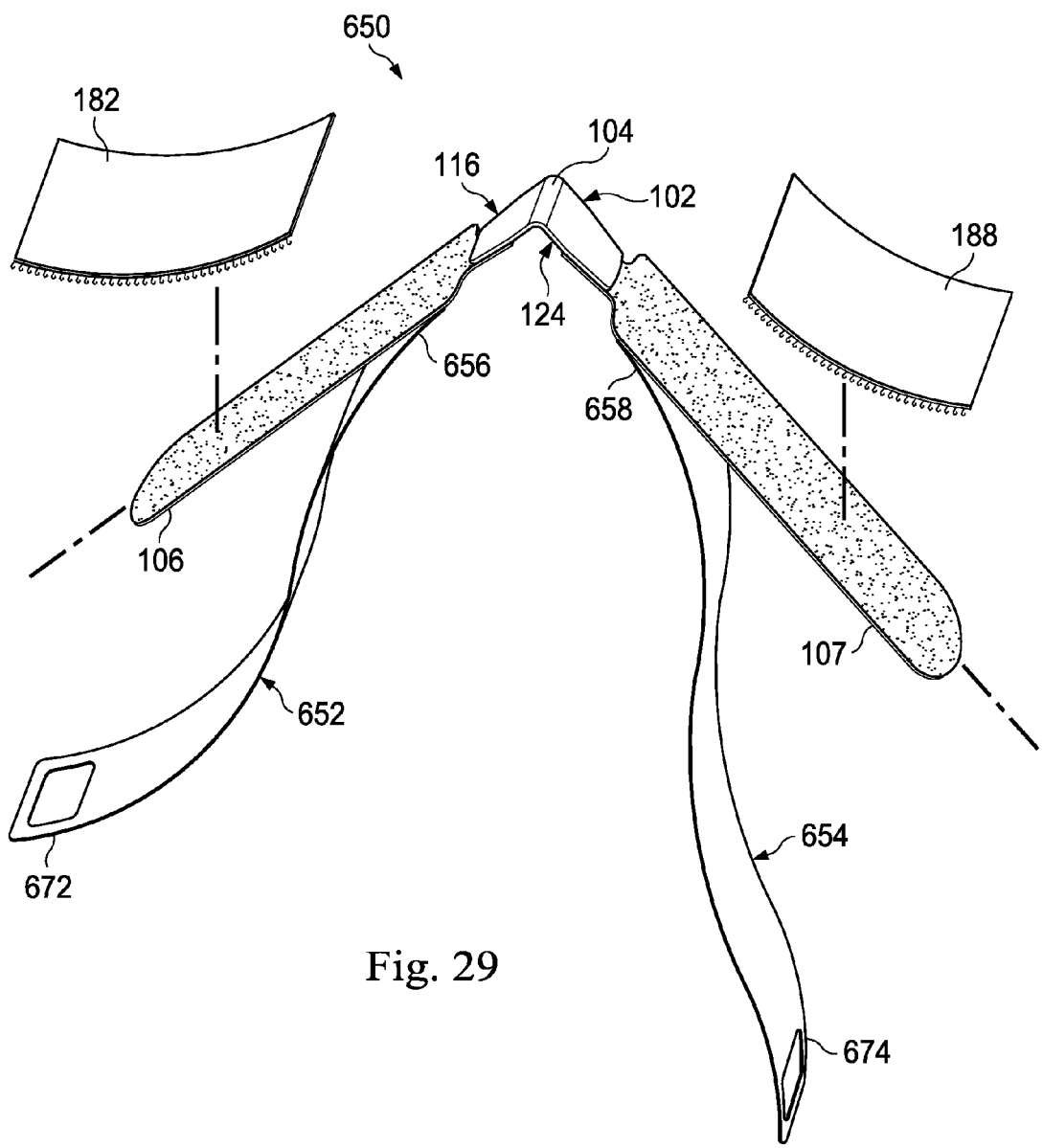
FIG. 29 is a perspective view of one aspect of the perianal support system according to an exemplary embodiment.
Figure 30:
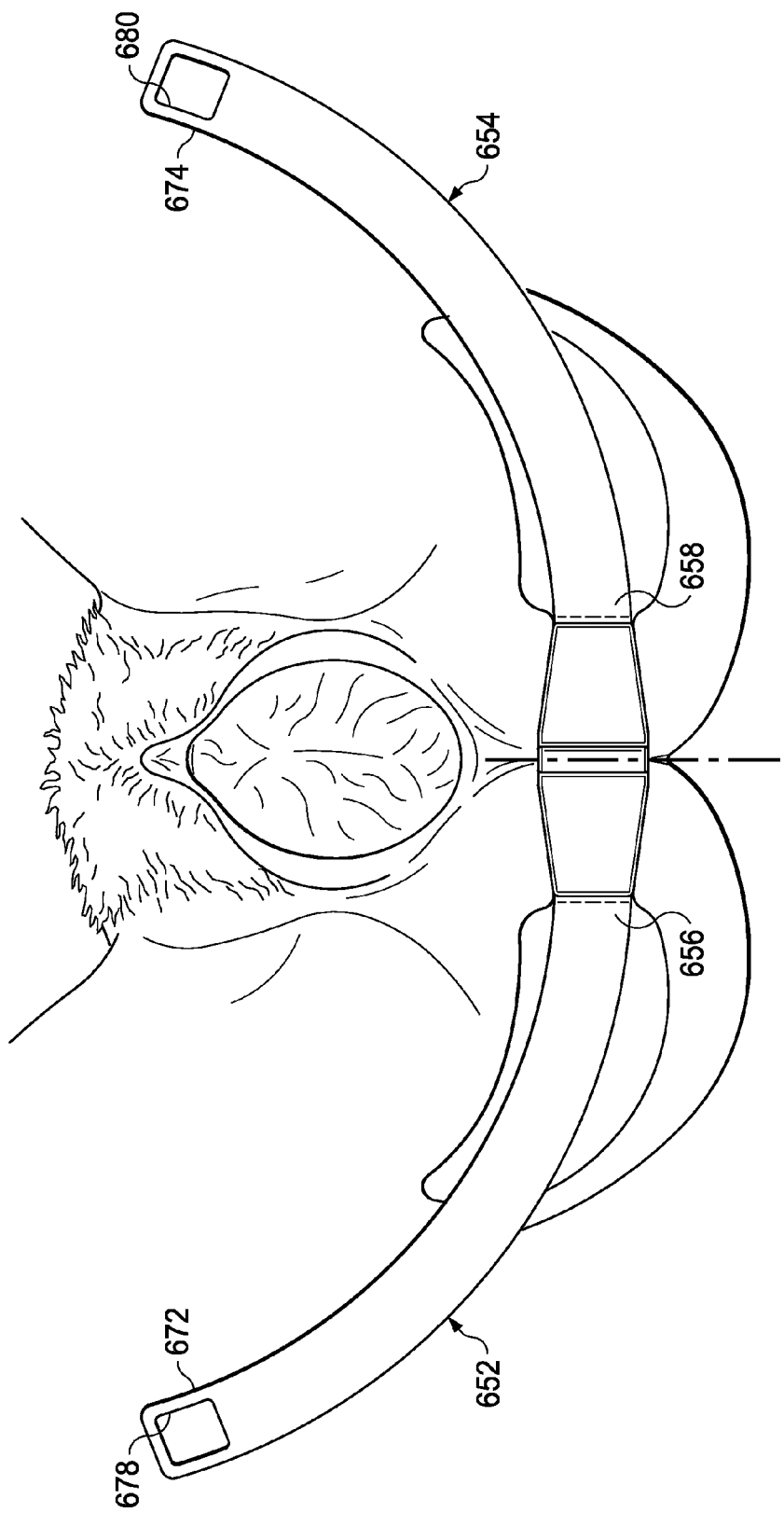
FIG. 30 is a partial perspective bottom view of the perianal support system applied to a patient during child delivery.

FIGS. 29 and 30 show yet another embodiment of a perianal support system, referenced by the numeral 650. This embodiment is similar in many ways to the support system 100 shown and discussed above, and may include any of the features or pressure detecting systems disclosed herein. Like the support system 100, the support system 650 includes the perianal support member 102 having the external pressure surface 104 and the securing members 106, 107 for attachment to a patient. In addition, the system 650 includes device adjustment elements 652, 654. The device adjustment elements 652, 654 extend from the perianal support member 102 or the securing members and are configured and arranged to permit the patient to adjust the support system 650. The adjustment may include modifying the pressure applied by the support system 650 on the perianal tissue or may include adjusting the physical location of the perianal support member 102 on the patient. Accordingly, during contractions or during pushing, the patient can apply additional pressure on the perianal tissue if desired. Therefore, the patient has some level of control of the pressure on the perianal tissue.

In this embodiment, the device adjustment elements 652, 654 are straps that extend from a location adjacent the perianal support member 102 in the same direction as the securing members 106, 107. These device adjustment elements 652, 654 may be flexible and may be substantially non-elastic so that the patient can easily pull the straps toward her head to increase the relative pressure on the perianal tissue or may release the tension in the straps to reduce the relative pressure on the perianal tissue. In the exemplary embodiment shown, the device adjustment elements 652, 654 respectively include a distal end 656, 658 and a proximal end 672, 674. The distal end 656 is disposed adjacent to or is connected to the proximal end portion of the compression element 116, and the distal end 658 is disposed adjacent to or is connected to the proximal end portion of the compression element 124.

The proximal ends 672, 674 each include a handle portion 678, 680 disposed therein that enable the patient to hold the device adjustment elements 652, 654. In the example shown, the handle portions 678, 680 are through holes in the device adjustment elements 652, 654 that enable a portion of the patient's hand or fingers to extend therethrough. In other embodiments, the handle portion is formed of a rolled distal end to provide a gripping portion. In yet other embodiments, the handle portion is coated with polyurethane or other friction enhancing material to allow the patient to comfortably grip the device adjustment elements 652, 654 and provide pressure.

The device adjustment elements 652, 654 extend from or adjacent the perianal support member 102 and are shaped and arranged to extend around the patients' flanks. The securing members 106, 107 may secure the support system 650 in place when the patient is not providing additional pressure loading. When additional pressure loading is desired, the patient may pull the device adjustment elements 652, 654 so that the device adjustment elements 652, 654 tighten around the patient's flanks and apply additional loading onto the perianal tissue. In the same manner discussed above, since the compression elements 116, 124 extend out beyond the crown of the buttocks, additional pulling on the straps by the patient results in an increase in pressure through the perianal support member 102 onto the perianal tissue of the patient. In some embodiments, the patient may monitor any of the pressure detecting systems described herein, and may adjust the support system using the device adjustment elements 652, 654 to maintain the applied pressure in a desired pressure range.

Figure 31:
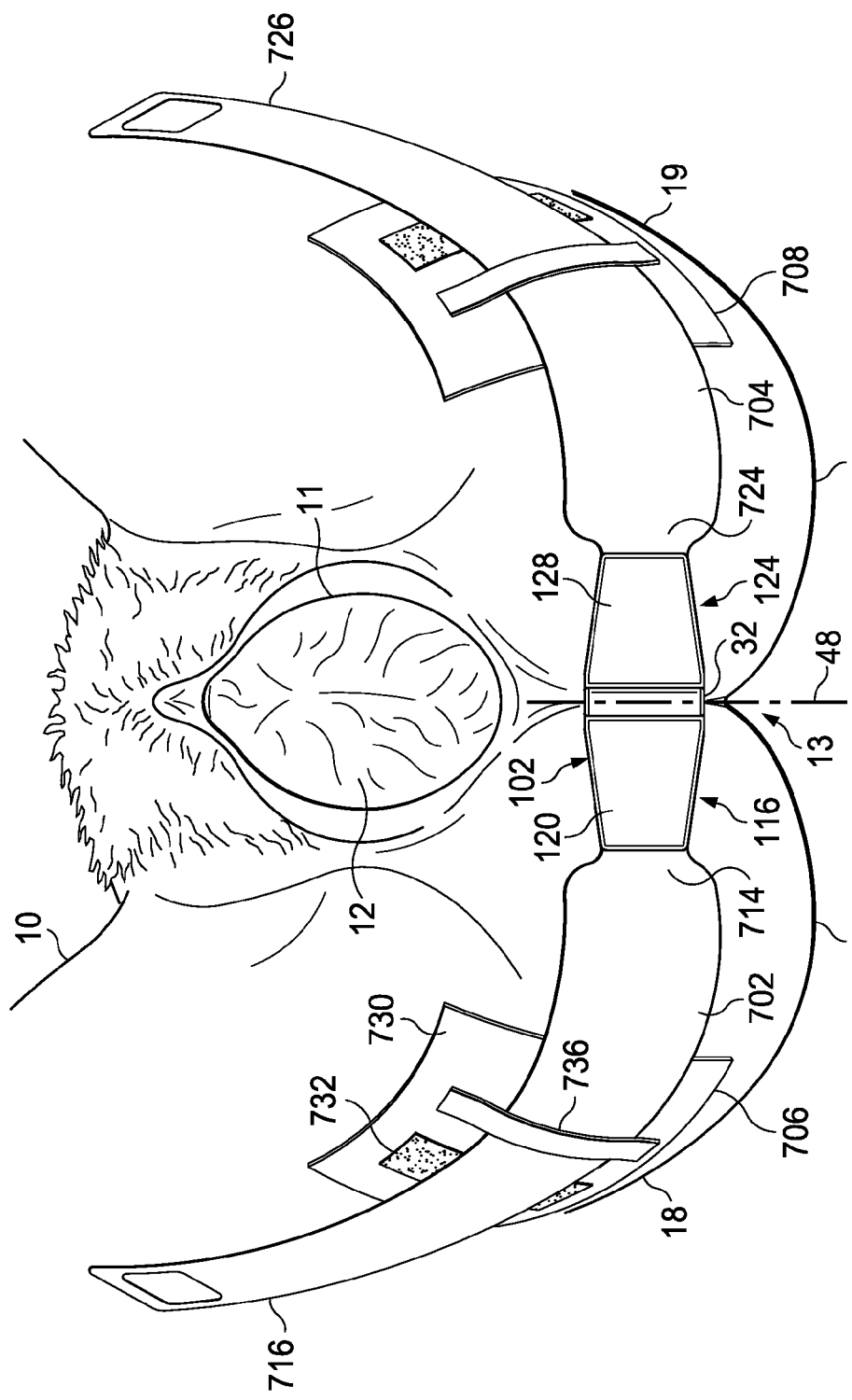
FIG. 31 is a perspective view of one aspect of the perianal support system according to an exemplary embodiment.

FIG. 31 shows an alternative embodiment of a perianal support system 700 using the perianal support member 102, but employing device adjustment elements that are integrated with the securing members. The support system 700 includes the perianal support member 102 as described above for supporting perianal tissue, device adjustment elements 702, 704, and anchor pads 706, 708.

The device adjustment element 702 has a distal end 714 and a proximal end 716. In the embodiment shown, the distal end 714 attaches to and extends from the proximal end portion 120 of the first compression element 116. Similar to the device adjustment element 652 described above, the device adjustment element 702 is an elongated strap and includes a handle portion 718 formed therein. The handle portion 718 may be formed in any manner, as discussed above. In this embodiment, the device adjustment element 702 includes a surface (facing away in FIG. 31) forming a first half of a fastening system. Here, the surface includes a fastening portion such as a hook and loop system or a releasable adhesive system.

The device adjustment element 704 is similar to the device adjustment element 702 and includes a distal end 724 and a proximal end 726. In the embodiment shown, the distal end 724 attaches to and extends from the proximal end portion 128 of the second compression element 124. Similar to the device adjustment element 702, the device adjustment element 704 is an elongated strap and includes a handle portion 728 formed therein. The handle portion 728 may be formed in any manner, as discussed above. In this embodiment, the device adjustment element 704 includes a surface (facing away in FIG. 31) forming a first half of a fastening system. Here, the surface includes a fastening portion such as a hook and loop system or a releasable adhesive system.

In this exemplary embodiment, the anchor pads 706, 708 are identical and only the anchor pad 706 will be described, recognizing that the description equally applies to the anchor pad 708. The anchor pad 706 includes an outer facing side 730 and an inner facing side (not shown in FIG. 31). The outer facing side 730 includes a fastening portion 732 configured to fasten to the fastening surface of the adjustment element 702. In this embodiment, the fastening portion is one of a hook or loop of a hook and loop fastener. The inner facing side is opposite the outer facing side 730 and is configured to interface with the patient. In one embodiment the inner facing side comprises an adhesive configured to adhere the anchor pad 706 to the patient's' skin, as discussed above. The anchor pad 706 also includes a guide 736 disposed thereon. The guide 736 is arranged to guide the device adjustment element 702 so that the distal portion 714 of the device adjustment element 702 is maintained in its lateral position while allowing the distal portion 714 to move in a substantially axial direction through the guide 736. In this embodiment, the guide 736 is a loop through which the device adjustment element 702 extends. However other embodiments include other types of guides.

The device adjustment elements in FIG. 31 allow a patient to quickly and easily adjust the position of the perianal support member 102 on the perianal tissue and to increase the pressure on the perianal tissue. In this embodiment, the patient may adjust the position or the pressure applied by the perianal support member 102 by manipulating the device adjustment elements 702, 704 relative to the anchor pads 706, 708. First, a health care provider may assist the patient by applying the perianal support member 102 in a proper position adjacent the perianal tissue on then patient, and with the device adjustment elements 702, 704 respectively fastened to the anchor pads 706, 708. The perianal support member 102 may be placed in a first therapeutic static pressure engaging position having a first pressure. The patient may then adjust the perianal support member 102 to apply a second, even higher pressure to resist contractions by laterally displacing the proximal ends of the device adjustment elements 702, 704 so that the inner fastening surfaces detach from the fastening portion 732 on the outer facing surfaces 730 of the anchor pads. With the device adjustment elements 702, 704 detached from the fastening portion 732, 734, the device adjustment elements may be axially displaced through the guides 736 to displace the perianal support member 102 in the lateral directions or to increase or decrease the pressure applied by the perianal support member 102 on the perianal tissue. When the perianal support member 102 is positioned as desired at the desired pressure, the patient may manipulate the device adjustment elements 702, 704 so that they reattach to the fastening portion 732 thereby securing the device adjustment elements and the perianal support member 102 in place on the patient. Again, the support system may be manipulated or adjusted as discussed herein to provide a desired pressure on the perianal tissue based on feedback provided by the pressure detecting systems.

Figure 32:
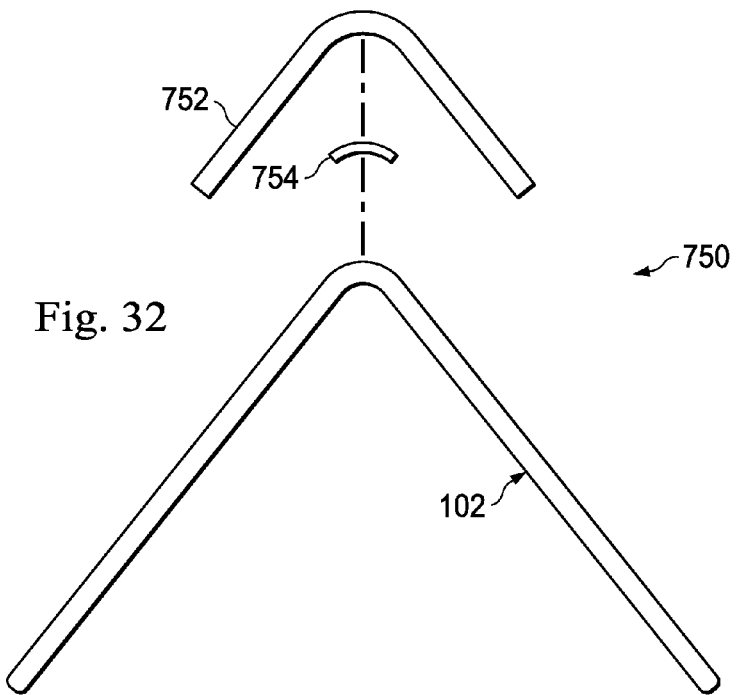
FIG. 32 is a view of a portion of another perianal support system according to an exemplary embodiment.

FIG. 32 shows a portion of yet another exemplary embodiment of a perianal support system 750 in accordance with an exemplary aspect of the present disclosure. The support system 750 may include the perianal support member 102 and the securing members 106, 107 as described herein. However, FIG. 32 shows an exploded view of a pressure detecting system 752 that comprises a pressure sensor 754 and a compliant pad 756. Here, the pressure sensor 754 is disposed between the pressure surface 104 and the compliant pad 756.

Figure 33:
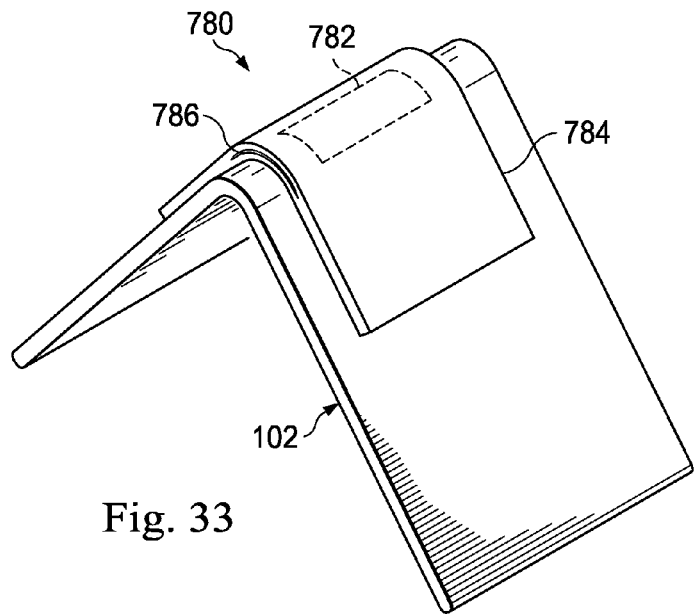
FIG. 33 is a view of a portion of another perianal support system according to an exemplary embodiment.

FIG. 33 shows a portion of yet another exemplary embodiment of a perianal support system 780 in accordance with an exemplary aspect of the present disclosure. The support system 780 may include the perianal support member 102 and the securing members 106, 107 as described herein. The support system 780 includes a pressure sensor 782 and a compliant pad 784. In this embodiment however, the pressure sensor 782 is disposed within the compliant pad 784. Here, the compliant pad 784 comprises a pouch or pocket 786 with an opening formed therein for receiving the pressure sensor 782. The pressure sensor 782 may be introduced to the compliant pad 784 in the birthing room or at the manufacturing facility. The pocket 786 may maintain the pressure sensor at the desired location to detect pressure applied against the perianal tissue.

Figure 34:
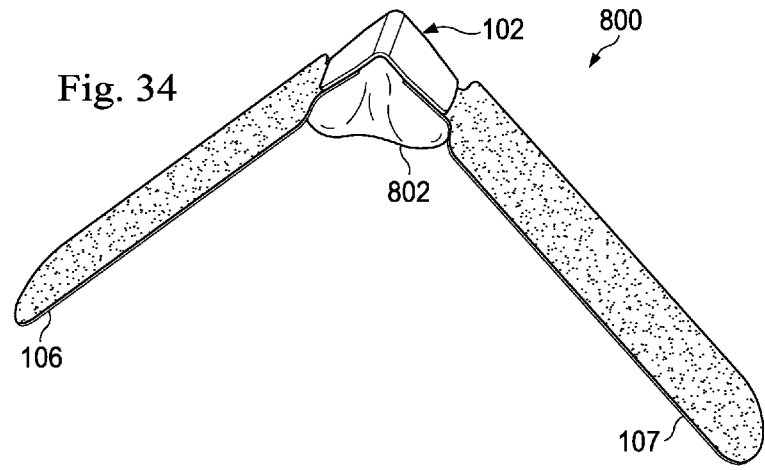
FIG. 34 is a view of a portion of another perianal support system according to an exemplary embodiment.

FIG. 34 shows yet another exemplary embodiment of a perianal support system 800 in accordance with an exemplary aspect of the present disclosure. The support system 800 may include the perianal support member 102 and the securing members 106, 107 as described above with reference to the support system 100 in FIGS. 1-6. In addition, the support system 800 includes a pliable receptacle or bag 802 disposed along the inner surface 132 in the area of the access cavity 136. In some examples, the pliable receptacle or bag 802 is a cooling applicator configured to receive and maintain a therapeutic cooling material, such as an ice, a frozen gel, or other ice-pack like material adjacent the perianal tissue. The pliable receptacle or bag 802 is configured to be opened, to receive the cooling material, and to be closed to maintain the therapeutic cooling material in place adjacent the perianal tissue. In some embodiments, the perianal support member 102 is formed of a thermally conductive material that may transfer at least a part of the temperature of the therapeutic cooling material to the perianal tissue to inhibit swelling and to provide cooling relief. In some embodiments, the pliable receptacle or bag 802 is configured to catch a placenta. In some embodiments, it is a V-shaped bag that is connectable to the perianal support member 102. In some examples, the perianal support member 102 holds an edge of the pliable receptacle or bag 802 tight against the patient's body, a position suitable for directly receiving the placenta as it is expelled from the patient's body.

Figure 35:
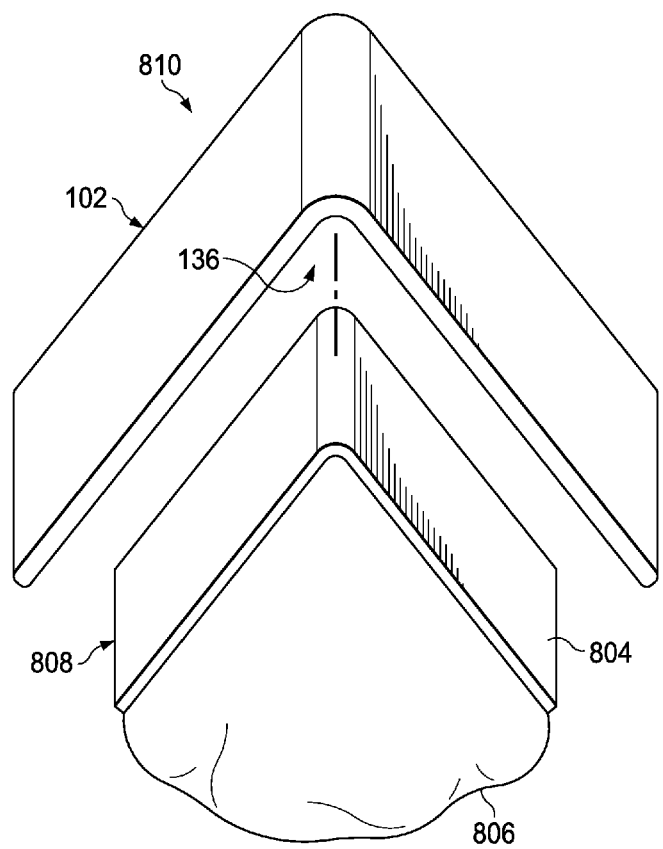
FIG. 35 is a view of a portion of another perianal support system according to an exemplary embodiment.

FIG. 34 shows the pliable receptacle or bag 802 that may form a cooling applicator 802 for receiving a cooling material or for capturing a placenta. FIG. 35 shows a perianal support system 810 having a cooling applicator 808 that comprises a cooling or ice pack formed to nest with the inner surface 132 in the access cavity 136 of the perianal support member 102. Accordingly, the cooling applicator 808 comprises a rigid thermally conductive surface portion 804 shaped to lie flush with at least an inner portion of the inner surface 132 of the perianal support member 102. A container portion 806 may extend from the conductive surface portion 804 and may be configured and arranged to hold the therapeutic cooling material. In some embodiments, the container portion 806 may be included on the receptacle or bag to form a placenta catcher in the manner discussed above. Accordingly, the placenta catcher may be attached to and may extend from support member 102.

Figure 36:
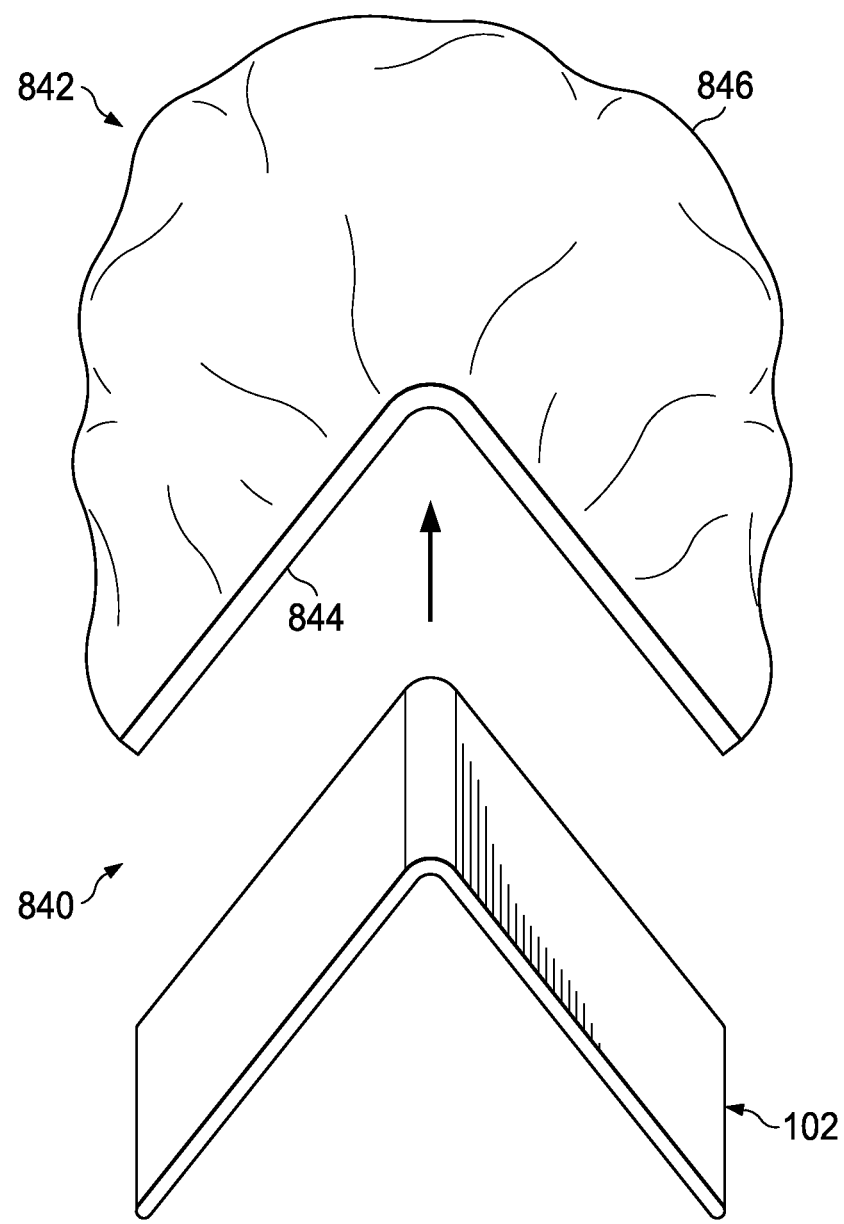
FIG. 36 is a view of a portion of another perianal support system according to an exemplary embodiment.

FIG. 36 shows yet another exemplary embodiment of a perianal support system 840 in accordance with an exemplary aspect of the present disclosure. This embodiment includes a cooling applicator 842 arranged to be disposed on the leading end of the perianal support member 102. In this embodiment, after the baby is removed from the patient, the healthcare provider may displace the perianal support member 102 a distance sufficient to place the cooling applicator 842 between the perianal support member 102 and the patient's perianal tissue. Accordingly, the perianal support system is used to support and maintain the cooling applicator 842 in a position to directly apply therapeutic cooling to the perianal tissue and the surrounding region.

In the embodiment shown, the cooling applicator 842 includes a connector support 844 and a cooling pack 846. The cooling pack 846 is configured to contain a therapeutic cooling material to provide relief to the perianal and surrounding tissue. The connector support 844 is configured to attach to or be carried by the perianal support member 102. In the embodiment shown, the connector support 844 is shaped to receive the surface portion of the perianal support member 102. The shaped connector support may help the perianal support member 102 maintain the cooling applicator 842 in place. In some embodiments, the cooling applicator 842 includes a fastening portion that fastens the cooling applicator 842 to the perianal support member 102. In some examples, the connector support 844 includes an adhesive surface that is configured to adhere to the perianal support member 102. Other examples include a hook and loop fastening strap that extends from the cooling pack to loop around the perianal support member 102 and to secure the cooling applicator in place. Yet other attachment fasteners are contemplated.

Perianal support devices as described herein may be applied to patients for a variety of reasons including, alone or in combination, any of the following: a) shortening second stage labor by providing a push focal point to enhance the effectiveness of contractions in advancing the baby down the birth canal, b) reducing the necessity of Cesarean section births by encouraging and monitoring, via pressure feedback, the effectiveness of contractions to generate a pushing effect on the baby to move it toward the vaginal opening as sensed by pressure exerted on the perianal tissue, c) covering all or most of the anal orifice and thereby providing defecation control, d) suppressing hemorrhoid development and/or advancement of existing hemorrhoids, and e) delivering post-delivery therapeutic treatments, such cooling treatments, for example.

Returning now to FIGS. 1 and 2, in use a health care provider positions the patient 10 to expose the perianal region 26. In the child birthing process, the patient 10 may be positioned in stirrups attached to a delivery table (not shown). The perianal support system 100 is then moved adjacent the gluteal cleft 13 between buttocks 14 and 15. The support system 100 is positioned such that the midline 108 of the perianal support member 102 is substantially aligned with the patient's midline within the sagittal plane. Referring to FIG. 1, the perianal support member 102 is advanced in the direction of arrow A1 toward the anal orifice 38 (generally within the sagittal plane toward the head of the patient) to bring the pressure surface 104 into contact with the perianal tissues. Continued advancement of the perianal support member 102 toward the anal orifice 38 applies pressure through the pressure surface 104 to the perianal tissues. In one aspect, the healthcare provider places at least one finger within the access cavity 136 and preferably against internal contact surface 170 to advance the device against the anal orifice 38. The healthcare provider utilizes a pressure feedback device associated with the perianal support device to sense that the initial placement exceeds a first pressure threshold. In one exemplary embodiment, the first pressure threshold is within a pressure range of about 0-770 mm of mercury. In one aspect, the initial positioning of the support device is spaced from or only in touching engagement without creating pressure when the patient is not experiencing a contraction. As a contraction occurs or the patient pushes, the perianal tissues will tend to protrude thereby engaging the device with a pressure that can be felt by the mother through tactile feedback and sensed by the pressure detection system. In still a further aspect, the pressure thresholds needed for adequate tactile sensation vary between patients such that the first pressure threshold may be in a range from 40-120 mm of mercury. In a further form, the second pressure threshold needed to enhance tactile sensation need only to be higher than the first pressure. In one aspect, the second pressure threshold can be in the range of 80-250 mm of mercury. With continued pressure applied by the healthcare provider to the access cavity 136, and/or internal contact surface 170, the elongate securing member 107 extends laterally of the anal orifice 38 away from the gluteal cleft 13 and is releasably attached to the patient 10 to at least the lateral flank 18. In a similar manner, with compressive force applied by the healthcare provider the perianal support member 102, the elongate securing member 107 extended laterally of the anal orifice 38 out of the gluteal cleft 13 and is secured to the patient adjacent lateral flank 19 to maintain the device on the patient in the static pressure therapeutic zone exceeding the first threshold. Thus, the securing members 106, 107 of the system 100 do not extend along the patient midline in the gluteal cleft 13 with the potential for interference with the birthing process, but instead extend substantially laterally from the patient's midline out of the gluteal cleft 13 and are attached at the patient's lateral flanks 18 and 19.

The extent of tissue deformation surrounding the anal orifice 38 when support system 100 is applied is a function of the patient anatomy and of the amount of compressive force applied during application of the support system 100. As shown in FIG. 1, the maximum extent of perianal tissue engagement inwardly on the patient in the saggital plane is shown by line 178. In one aspect, it is contemplated that pressure applied in the direction of arrow A1 moves the anal orifice inwardly 1 cm to 3 cm. In one embodiment, the lateral ends 144, 146 of the securing members 106, 107 extend beyond line 178 generally in the patient's saggital plane. The securing members 106, 107 exert tension forces generally in the direction of arrows A2 and A3, respectively. This tension force is applied to compression elements 116, 124, which are substantially rigid members capable of transmitting compressive forces to the perianal support member 102. The tension force applied on the lateral flanks 18 and 19 of the patient 10 in the direction of arrows A2 and A3 is converted to compressive forces in the direction of arrows A4 and A5, respectively. The compressive forces A4 and A5 are transmitted by substantially rigid compression elements 116, 124 and ultimately to the pressure surface 104 to apply support and/or pressure to the perianal tissues in the direction of arrow A1. It will be appreciated that the lateral components of compressive forces applied in A4 and A5 helps to maintain the position of the perianal support member 102 as well as tending to maintain access cavity 136 in an open position.

Still referring to FIGS. 1 and 2, each compression element 116, 124 has a length L1 and extends away from each other by an angle A1. The maximum lateral distance of the access cavity is defined by the distance D1 extending between distal end portions 120, 126. In one embodiment, L1 is greater than 4 cm in length. In a preferred aspect, L1 is approximately 8 cm. In one embodiment angle A1, is between 140 degrees and 30 degrees. In the illustrated embodiment, angle A1 is approximately 80 degrees. In one embodiment, the maximum lateral distance D1 of the access cavity 136 is greater than 4 cm. In the illustrated embodiment of FIG. 1, the maximum lateral distance is approximately 10 cm. It will be understood that while compression elements 116, 124 are sufficiently rigid to transmit compressive force toward the pressure surface, in one embodiment they are flexible, at least laterally, to bow or bend in response to force applied to the securing members 106, 107. In contrast, the anterior to posterior distance of the pressure surface 104 between the first edge 110 and second edge 112 is approximately 5 cm in the illustrated embodiment. This midline length between the first edge 110 and the second edge 112 of the perianal support member 102 can be adjusted in some embodiments depending on the amount and extent of perianal tissue that needs to be supported.

The distance D2 between the anal orifice and the buttocks crown 16 is less than the distance D3 between the distal end 64 of the flange 60 and the anal orifice. Thus, tension applied to securing members 106, 107 is transferred through substantially rigid compression elements 116, 124, to exert a compressive force on pressure surface 30 in the direction of arrow A1. Whereas, if distance D2 is greater than distance D3 tension applied to securing members 106, 107 may pull the perianal support member 102 in a direction opposite arrow A1.

It will be appreciated that with the illustrated embodiment, the healthcare provider may reposition the perianal support member 102 and adjust the compressive force applied through the securing members 106, 107 to the pressure surface 104 by releasing or adjusting the attachment between the securing members 106, 107 and the patient 10.

Additionally, in the illustrated embodiments, the perianal support member of the support systems is sized and positioned with respect to patient 10 to allow for the passage of a child through the birthing canal during childbirth. It is contemplated that the perianal support member may be placed to support more or less of the perineum between the anus and vaginal opening depending on the health care provider's judgment and the progress of the child birthing process. Still further, it is contemplated that an elongated anterior to posterior device may be positioned to support at least a portion of the perianal tissue and the vaginal tissue during the labor process. It is anticipated that the supporting device will be repositioned posteriorly away from the vaginal opening prior to delivery of the child through the vaginal opening.

Figure 37:
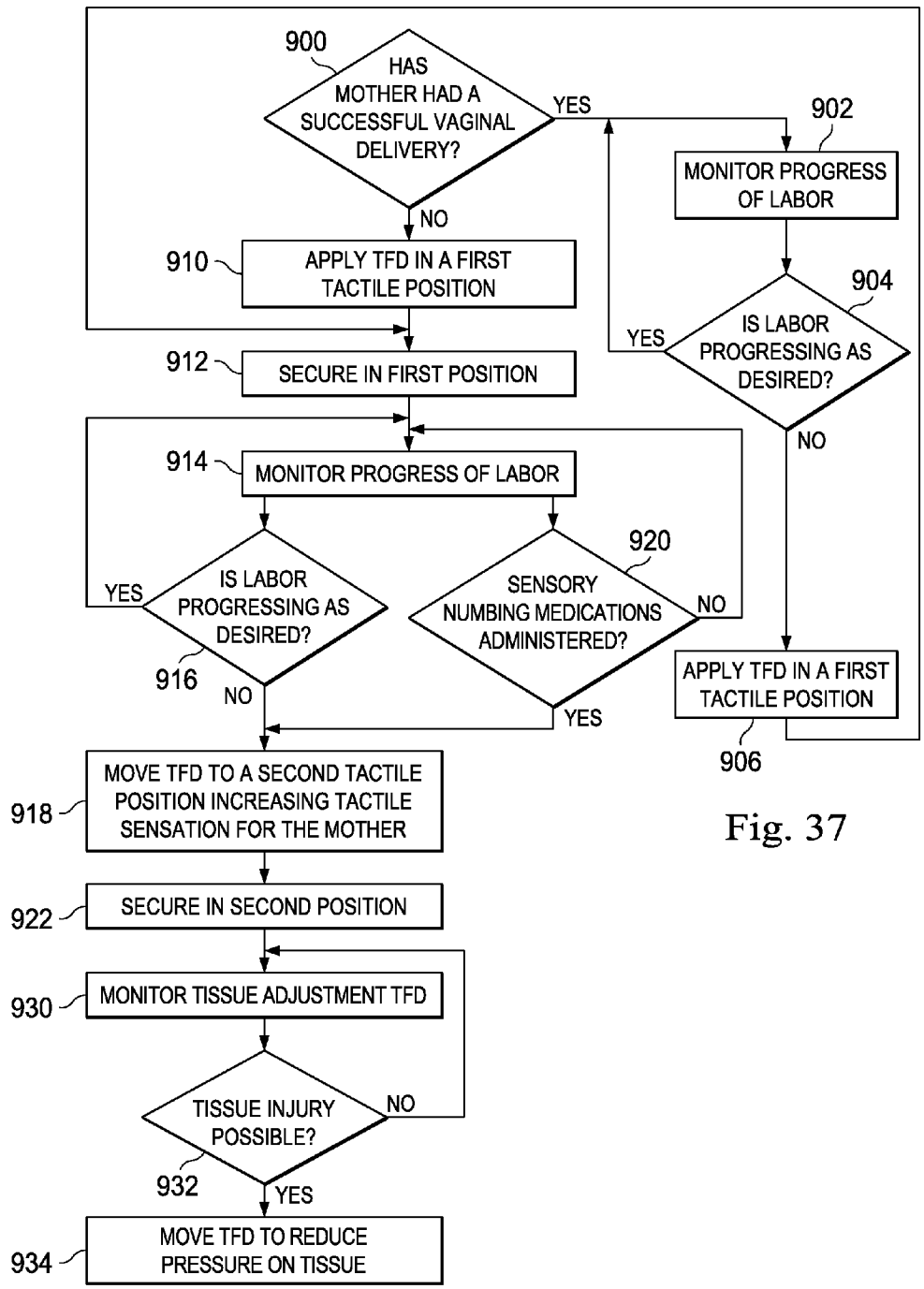
FIG. 37 illustrates a method of managing a mother's child birthing labor according to an exemplary embodiment.

In use, a health care provider positions the patient to expose the perianal region and vagina. Referring now to FIG. 37, there is a shown a flow chart illustrating a method of utilizing a labor management device according to one aspect of the present disclosure to manage a mother's labor process to reduce the duration of second stage labor and increase the incidence of a vaginal delivery without increasing tissue damage to the mother. In general terms, the method includes applying a tactile feedback device in engagement with the perianal tissue and monitoring the progression of labor during the second stage. With respect to FIG. 37, the method begins at step 900 by determining whether the expecting mother has previously delivered a child by a vaginal delivery. If the answer to this inquiry is yes, then at step 902, the progress of labor is monitored to determine if labor is progressing as desired at step 904. In one instance, the progression of labor can include the amount of movement of the child toward the vaginal opening over a given a period of time. In another instance, the progression of labor can include shortening or thinning of the cervix, the amount of cervical dilation, digital (finger) assessment of fetal position, assessment of fetal decent, the amount of movement of the child toward the vaginal opening in comparison to the number of contractions or successful pushes the mother has experienced. The determination of the progression of labor may be made by a healthcare provider monitoring the patient or by an electronic monitoring system receiving one or more inputs indicative of labor progression such as the number of contractions, effective pushes, and movement of the child within the mother and/or overall time of labor. As long as labor is progressing as desired, the method continues with monitoring the progress of labor. If labor is not progressing as desired in step 904, then the method progresses to the application of a tactile feedback device (TFD) in a first tactile position at step 906 which could include devices similar to any of the device embodiments described above or any other device configured and applied to provide perianal tactile sensation to the patient. A first tactile position can include applying a TFD in a pressure inducing and tissue compression engagement at a first pressure threshold, engagement with the perianal tissue without pressure inducement or tissue compression, or positioning adjacent the perianal tissue sufficiently close such that during a push by the mother, the protrusion of soft perianal tissue will engage the TFD to provide a tactile sensation to the mother. Once the TFD is positioned in the desired first tactile position, the method includes the step at 912 of securing the TFD to the mother in the first position.

During initialization of the method in step 900, if it is determined that the mother has not previously had a successful vaginal delivery or has previously undergone a Cesarean section child delivery procedure, the method continues to step 910 where a TFD is applied in a first tactile position to provide perianal tactile sensation to the mother. Of course, use of the methods and devices described above can be applied to all patients; however, it may be desirable in some situations to limit use of the labor management devices and techniques to those patients mostly likely to benefit from the added attention and treatment. As described above, a first tactile position can include applying a TFD in a pressure inducing and tissue compression engagement at a first pressure threshold, engagement with the perianal tissue without pressure inducement or tissue compression, or positioning adjacent, but spaced from, the perianal tissue in a sufficiently close arrangement such that during a push by the mother, the protrusion of soft perianal tissue will engage the TFD to provide a tactile sensation to the mother. Once the TFD is positioned in the desired first tactile position, the method includes the step at 912 of securing the TFD to the mother in the first position in any suitable manner, including the secure techniques disclosed herein.

After the TFD is positioned, the method of using a TFD to manage a mother's labor continues at step 914 by monitoring the progress of labor. In one instance, the progression of labor can include shortening or thinning of the cervix, the amount of cervical dilation, the amount of movement of the child toward the vaginal opening over a given a period of time. In another instance, the progression of labor can include the amount of movement of the child toward the vaginal opening in comparison to the number of contractions or successful pushes the mother has experienced. As mentioned above, the TFD may include a counting component to track the number of successful pushing episodes experienced by the device. The determination of the progression of labor may be made by a healthcare provider monitoring the patient or by an electronic monitoring system receiving one or more inputs indicative of labor progression such as the number of contractions, effective pushes, and movement of the child within the mother and/or overall time of labor. As long as labor is progressing as desired in step 916, the method continues with monitoring the progress of labor in step 914. If labor is not progressing as desired in step 916, then the method progresses to modifying the position of the TFD at step 918 to move the TFD to a second tactile position on the mother to thereby increase the tactile sensation for the mother. Similarly, the monitoring of the labor process also takes into account the administration of sensory numbing medications administered to the mother at step 920. As will be appreciated, the application of numbing medications, including spinal epidurals, orally administered pain relievers and intravenously injected pain relievers, may significantly reduce the mother's ability to feel pain along with tactile sensation in the perianal tissues. As a result, the method of managing the labor process advances to step 918 to increase the amount of tactile sensation applied to the perianal tissues.

In one aspect, in order to increase tactile sensation at step 918, the TFD is moved to a second tissue engaging position where the amount of pressure applied to the perianal tissue is increased compared to the first tactile position. In an exemplary embodiment, the TFD includes a pressure indication mechanism that provides feedback to the individual moving the device about how pressure is being applied, or if the pressure is increasing from the first position, as the TFD is moved to the second position against the perianal tissues. In an alternative form, the healthcare provider applies inward (toward the anus) movement of the TFD while receiving feedback from the mother concerning her ability to sense the increased tactile sensation. Once the mother indicates a desired level of tactile sensation, the healthcare provider (or the patient in patient manipulated embodiments) secures the device in the second position at step 922. As will be appreciated, the process of monitoring labor in step 914 and increasing the tactile sensation (or managing the labor process to decrease the tactile sensation if the mother experiences excessive pain) can be repeated multiple times throughout the labor process to manage a balance between causing pain/injury to the mother and provides the mother with a tactile sensation to push against to generate more effective pushes with increased movement of the child into and through the birth canal. More specifically, at step 930, tissue adjacent the TFD is monitored to avoid applying too high a pressure on the tissue for too long of a time period. Thus, in step 932 if it is determined that the current position of the TFD may cause tissue injury, then in step 934 the TFD device can be moved to reduce the pressure on the perianal tissue. In one embodiment, the TFD includes a mechanism for alerting the user to an over pressure situation and this mechanism can provide feedback on the force exerted on the perianal tissue.

The above described labor management method may be implemented in a variety of child birthing processes, however in a typical child birthing process, the patient may be positioned in stirrups attached to a delivery table. If used, anchor pads 182, 188 are adhered to the patient's skin on the lateral flanks 18 and 19, respectively. As best seen in FIG. 2, the anchor pads 182, 188 are positioned on the lateral flanks 18 and 19 laterally adjacent the junction of the femur with the pelvis. The perianal support device 100 is then moved adjacent the gluteal cleft 13 between buttocks 14 and 15. The midline 48 of the support device is generally aligned with the patient midline within the sagittal plane. The support device is advanced in the direction of arrow A1 toward the anal orifice 38 (generally within the sagittal plane) to bring the perianal support member 102 into contact with the perianal tissues. Continued advancement of the support device toward the anal canal applies pressure through the pressure surface 104 to the perianal tissues. In one aspect, the healthcare provider places at least one finger within the access cavity 136 and preferably against internal contact surface 170 to advance the device against the anal orifice. In another aspect, an instrument having complimentary engagement surface to at least a portion of the access cavity 136 is used to apply pressure to the device 100. The healthcare provider may then observe the pressure detecting system as disclosed herein to determine whether a suitable pressure is being applied to the device. If more pressure is desired as indicated by the pressure detecting system, then the healthcare provider may provide additional pressure.

With continued pressure applied by the healthcare provider to the access cavity 136, and/or internal contact surface 170, elongated securing member 106 is extended laterally of the anal orifice 38 out of the gluteal cleft 13 and releasably attached to anchor pad 182 with at least lateral end 144 extending adjacent lateral flank 19. In a similar manner, with compressive force still applied by the healthcare provider to support device 100, elongate securing member 107 is extended laterally of the anal orifice 38 out of the gluteal cleft 13 and is secured to anchor pad 588 with at least lateral end 146 extending adjacent lateral flank 18. In embodiments employing pressure detecting systems in the securing members to determine whether a suitable pressure is being applied to the device, the healthcare provider may visually observe the securing members or may be able to identify by tactile feedback when a suitable pressure is applied by the support system 100. If more pressure is desired as indicated by the pressure detecting systems, then the healthcare provider may provide additional pressure. The fixation members 106, 107 of the system 100 do not extend along the gluteal cleft 13 with the potential for interference with the birthing process but instead extend substantially laterally from the patient's midline out of the gluteal cleft 13. In embodiments having device adjustment elements that may be manipulated by the patient, the patient may adjust the pressure applied by the system based on feedback from the pressure detecting systems.

The extent of tissue deformation surrounding the anal orifice 38 is a function of the patient anatomy and of the amount of compressive force applied during application of the support device 100. In one aspect, the health care provider makes initial contact with anal orifice 38 and then applies pressure in the saggital plane (generally toward the patient's head) to advance the device 1 cm to 3 cm. This advancement of the device approximately 1 cm to 3 cm compresses the perianal tissue and thereby supports the tissue to inhibit distention as the patient pushes during the birthing process. It will be appreciated that with the illustrated embodiment, the healthcare provider may reposition the device and adjust the compressive force applied through the compression members 106, 107 to the pressure surface 104 by releasing or adjusting the attachment between the anchor pads 182, 188 and the fixation members 106, 107.

In an alternative approach, the pressure surface 104 is positioned in engagement with the anal orifice with little if any compressive force applied to deform the perianal tissue. The support device is then secured in position as described above. With this technique, the support device will resist movement of the device in a direction generally away from the patient's head and will thereby support the perianal tissue to maintain its position. In a further feature, a pressure feedback device may indicate outward pressure on the perianal tissue to provide feedback to the patient on successful pushing during contractions.

Still referring to FIG. 1, with system 100 in position, a healthcare provider is allowed to position one or both hands within the access cavity 136 extending into the gluteal cleft. In this manner, the hands may be below the lowest portion of the vaginal opening 11 as the head of the baby 12 passes out of the vagina. Thus, the hand within the access cavity 136 is positionable less than 1 cm from the mother's vaginal opening or perineum so the healthcare provider may support the head of the baby as is it is being born. The position of second edge of the support device 100 also allows access to the tissue immediately below the vaginal opening 11 in the event an obstetric maneuver, such as an episiotomy, manipulation of the fetus, etc., is necessary. Further, as discussed above, in one aspect the perianal support member 102 is quickly repositioned or removed by releasing at least one of the straps from the anchor pads, an obstetric maneuver is performed, the perianal support member 102 is repositioned in a supporting position adjacent the anus and the anchoring straps are repositioned on the anchor pads. Therapeutic cooling may be applied by attaching or securing a cooling applicator in place using the system 100.

In one embodiment, the support system is formed of biocompatible material suitable for contact with human tissue. Moreover, in one embodiment, the device is provided sterile in a package for single use application on a patient, although reusable devices according to the present teachings are also disclosed in the present description. In the single use type of embodiment, the device is cost effectively manufactured such that it is discarded after use. For example, the device 100 is formed by of a substantially rigid polycarbonate material. In one aspect, the device 100 is injection molded to substantially its final V-shaped form. The compliant pad is then applied to the apex and securing members are joined to the compression members via an adhesive. It is contemplated that securing members 106, 107 may be riveted, snapped or otherwise fixedly attached to the compression elements. Still further, in a different embodiment, the securing members are passed through a channel or other opening associated with the compression elements to loosely and/or removably join the securing member to the perianal support member 102. In one aspect, compression elements comprise a loop portion of a hook and loop fastening system, such as sold under the tradename VELCRO.

It is contemplated that in other embodiments, the perianal support member 102 is formed by compression molding, transfer molding, reactive injection molding, extrusion, blow molding, casting, heat-forming, machining, deforming a sheet, bonding, joining or combinations thereof. In other embodiments, suitable materials for device 300 include polymers, metals, ceramics or combinations thereof. The materials can be or include alone or in combination: hard solids, soft solids, tacky solids, viscous fluid, porous material, woven fabric, braided constructions, or non-woven mesh. Examples of polymers include polyethylene, polyester, Nylon, Teflon, polyproplylene, polycarbonate, acrylic, PVC, styrene, PEEK, etc. Examples of ceramics include alumina, zirconia, carbon, carbon fibers, graphites, etc. Examples of suitable metals include titanium, stainless steel, cobalt-chrome, etc.

It is contemplated that in still further embodiments, the complaint pad can be made from or includes at least one of the following, either alone or in combination: woven fabric, non-woven mesh, foam, film, porous sheet, and non-porous sheet. At least the perianal support member 102 and compliant pad are sterilized by known techniques; such as ethylene oxide gas, gas plasma, electron-beam radiation or gamma radiation. Such materials are available from various suppliers such as 3M. In a similar manner, the fixation members or straps may be formed of hook and loop fastening systems available from 3M. Adhesive fixation systems may be adhesive a Rayon woven tape on a liner (1538L from 3M). The tape may include liners to prevent premature tape adhesion. In one embodiment, the liners include a cut between the midline end adjacent device 300 and the lateral end. During initial placement, the device is pushed against the anus with a first hand. The opposite hand spreads the buttocks away from the device while the first hand pushes the perianal support member to get further compressive penetration in the gluteal cleft. The hands are switched and the steps are repeated on the opposite buttocks. After position the device, the liners adjacent the device are sequentially removed and adhered to the medial portion of the buttocks for provisional positioning of the device. Once the device is provisionally positioned, the first lateral liner is removed and with pressure applied to the device, the lateral tape segment is adhered to the patient in a final supporting position to supply compressive force to the device. This step is repeated on the opposite side for final fixation.

The present invention also contemplates a kit that includes one or more of the components described above provided in a package. In one embodiment, the kit includes at least a sterilized perianal support device. In another aspect, the kit further includes an anchoring assembly as described above. In another aspect, the kit includes a pressure detecting system. In another aspect, the kit includes a patient adjustment system. In some embodiments, the anchoring assembly may be preassembled with the perianal support device as shown in the drawings or may be provided unassembled. In the unassembled kit, a health care provider will remove the support device and anchoring assembly from the packaging and assembly the support device with the anchoring assembly and the pressure detecting system. As set forth above, the anchoring assembly may be adhered to the support assembly near the patient or the support assembly may include fastening members or apertures to receive elements of the anchoring assembly. For example, the support device may include an aperture and a portion of a flexible strap may be threaded through the aperture to join the two components. In still a further embodiment, the kit includes a treating compound to apply to the patient. In one such embodiment, the treating compound is provided in a separate package. In an alternative embodiment, the treating compound is applied to or incorporated into the support device on the perianal contact surface.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure. Furthermore, although elements of the described embodiments may be described or claimed in the singular, the plural is contemplated unless limitation to the singular is explicitly stated. Additionally, all or a portion of any aspect and/or embodiment may be utilized with all or a portion of any other aspect and/or embodiment.

What is claimed is:

1. A child birth labor pelvic floor support apparatus, comprising:
    a support member comprising:
        a pressure surface configured to apply pressure on tissue adjacent a pelvic floor of a patient to support the pelvic floor during child birth;
        a compression element extending in a direction from the pressure surface and configured to convey applied loading toward the pressure surface to maintain the pressure surface in a position that applies the pressure on the tissue to support the pelvic floor; and
    a pressure detecting system configured to detect pressure on the tissue adjacent the pelvic floor of the patient.

2. The childbirth labor pelvic floor support apparatus of claim 1, wherein the pressure detecting system comprises:
    a pressure detecting element configured to detect pressure applied on the tissue adjacent the pelvic floor by the pressure surface; and
    a user interface configured to display information relating to the pressure detected by the pressure detecting element.

3. The childbirth labor pelvic floor support apparatus of claim 2, wherein the user interface is configured to wirelessly communicate with the pressure detecting element.

4. The childbirth labor pelvic floor support apparatus of claim 1, wherein the pressure detecting system comprises a compliant pad on a pressure surface of the childbirth labor pelvic floor support apparatus and the compliant pad is configured to change appearance when the pressure exceeds a threshold pressure.

5. The childbirth labor pelvic floor support apparatus of claim 1, wherein the tissue adjacent the pelvic floor includes at least a portion of a perineum between an anus and a vaginal opening of the patient.

6. The childbirth labor pelvic floor support apparatus of claim 1, wherein the pressure detecting system comprises:
    a securing member extending from the childbirth labor pelvic floor support apparatus, the securing member being configured to convey information indicative of the pressure applied on the tissue adjacent the pelvic floor adjacent an anal orifice of the patient by the pressure surface.

7. The childbirth labor pelvic floor support apparatus of claim 6, wherein the securing member comprises an element configured to change appearance when pressure changes.

8. The childbirth labor pelvic floor support apparatus of claim 1, further comprising a counter associated with the pressure detecting system, the counter configured to count pressure sequences above a first threshold indicative of effective pushes of the patient during child birth labor.

9. The childbirth labor pelvic floor support apparatus of claim 1, wherein the compression element comprises:
    a first rigid compression element surface disposed to face a first buttock in a gluteal cleft of the patient in response to the pressure surface being disposed adjacent an anal orifice of the patient, the first compression element surface extending away from the pressure surface in a first direction out of the gluteal cleft; and
    a second rigid compression element surface disposed to face a second buttock in the gluteal cleft of the patient in response to the pressure surface being disposed adjacent the anal orifice, the second compression element surface extending away from the pressure surface in a second direction out of the gluteal cleft.

10. A child birth labor management apparatus, comprising:
    a tissue engagement portion configured to apply pressure on tissue adjacent a pelvic floor of a mother in child birth labor;
    a load transfer portion configured to convey an applied load to the tissue engagement portion; and
    a user interface configured to present information relating to a pressure level applied by the tissue engagement portion on the tissue adjacent the pelvic floor of the mother as a result of the applied load.

11. The child birth labor management apparatus of claim 10, wherein the load transfer portion comprises:

first and second surfaces formed of one or more rigid compression elements extending away from the tissue engagement portion in a direction out of a gluteal cleft of the mother.

12. The child birth labor management apparatus of claim 10, wherein the user interface comprises:
   a securing member attached to and extending from the child birth labor management apparatus, the securing member being configured to convey information indicative of pressure applied on the tissue adjacent the pelvic floor of the mother by the tissue engagement portion.

13. The child birth labor management apparatus of claim 12, wherein the securing member comprises an elastic strap arranged to stretch and generate the applied load on the load transfer portion.

14. The child birth labor management apparatus of claim 10, wherein the user interface comprises a display screen configured to present information to a user indicating pressure on the tissue adjacent the pelvic floor of the mother.

15. The child birth labor management apparatus of claim 10, wherein the user interface comprises:
   a load detecting element connected to the child birth labor management apparatus and configured to detect a load indicative of pressure applied by the tissue engagement portion on the tissue adjacent the pelvic floor of the mother; and
   a display element associated with the load detecting element to convey the detected load to the user.

16. The child birth labor management apparatus of claim 15, wherein the load detecting element comprises a pressure sensor.

17. The child birth labor management apparatus of claim 15, wherein the load detecting element comprises a pressure responsive pad and the display element comprises a portion of the pad that is configured to change color when a pressure threshold is exceeded.

18. The child birth labor management apparatus of claim 15, wherein the load detecting element comprises a strain gauge.

19. The child birth labor management apparatus of claim 10, wherein the user interface comprises a pressure switch configured to complete an electrical circuit when the pressure level applied by the tissue engagement portion on the tissue adjacent the pelvic floor of the mother is above a threshold level.

20. A pelvic floor support device, comprising:
   an external pressure portion configured to engage tissue adjacent the pelvic floor of a patient during child birth labor;
   a compression element configured to provide a load to the external pressure portion to maintain the external pressure portion engaged with the tissue with a pressure amount; and
   a pressure detection system configured to detect the pressure amount.

21. The pelvic floor support device of claim 20, wherein the compression element comprises:
   a first compression element extending at a first angle from the external pressure portion in a first direction; and
   a second compression element extending at a second angle from the external pressure portion in a second direction, the first and second angles being approximately equal and the first and second directions being different from each other.

22. The pelvic floor support device of claim 20, wherein the pressure detection system comprises:
   a pressure detection pad coupled to the external pressure portion such that the pressure detection pad rests between the tissue and the external pressure portion, the pressure detection pad comprising an internal cushioning structure.

23. The pelvic floor support device of claim 22, wherein the pressure detection pad comprises:
   a friction surface that comes in contact with the tissue; and
   a treating compound disposed with the pressure detection pad.

24. The pelvic floor support device of claim 20, wherein the pressure detection system is configured to dynamically display a color indicative of the pressure amount, wherein different colors are associated with different therapeutic pressure levels.

25. The pelvic floor support device of claim 20, further comprising:
   a cooling pack comprising a therapeutic cooling material, the cooling pack being configured to attach to a surface of the external pressure portion and come in contact with the tissue adjacent the pelvic floor to provide relief to the contacted tissue.

26. A pelvic floor support device, comprising:
   a pressure surface configured to engage tissue adjacent the pelvic floor of a patient during child birth labor;
   a compression element configured to provide a load to the external pressure surface to maintain the external pressure surface engaged with the tissue with a pressure amount; and
   a pressure sensor configured to detect the pressure amount.

27. The pelvic floor support device of claim 26, further comprising:
   a transmitter disposed beneath a surface of the pressure surface, the transmitter being in communication with the pressure sensor and configured to:
      receive, from the pressure sensor, a signal indicative of the pressure amount detected by the pressure sensor; and
      transmit the received signal to a separate receiver that is remote from the transmitter and configured to display information based on the received signal to a user.

28. The pelvic floor support device of claim 27, wherein the separate receiver comprises a mobile communication device associated with the user.

29. The pelvic floor support device of claim 26, wherein the pressure sensor comprises:
   a strain gauge coupled to the compression element and configured to detect strain in the compression element during the child birth labor; and
   a transmitter configured to transmit the detected strain representative of the pressure amount to a user interface.

30. The pelvic floor support device of claim 26, further comprising:
   a light in communication with the pressure sensor, wherein the light is configured to:
      output a first color in response to the pressure amount exceeding a first threshold level;
      output a second color in response to the pressure amount exceeding a second threshold level; and
      output a third color in response to the pressure amount exceeding a third threshold level,
   wherein the second threshold level is greater than the first threshold level and the third threshold level is greater than the second threshold level.

* * * * *